US010660586B2

(12) United States Patent
Choy et al.

(10) Patent No.: US 10,660,586 B2
(45) Date of Patent: May 26, 2020

(54) RADIATION THERAPY SYSTEMS THAT INCLUDE PRIMARY RADIATION SHIELDING, AND MODULAR SECONDARY RADIATION SHIELDS

(71) Applicant: The Board of Regents of the University of Texas System, Austin, TX (US)

(72) Inventors: Hak Choy, Dallas, TX (US); Steve Jiang, Dallas, TX (US); Robert Timmerman, Westlake, TX (US); Arnold Pompos, Irving, TX (US)

(73) Assignee: The Board of Regents of the University of Texas Systems, Austin, TX (US)

( * ) Notice: Subject to any disclaimer, the term of this patent is extended or adjusted under 35 U.S.C. 154(b) by 0 days.

(21) Appl. No.: 16/443,360

(22) Filed: Jun. 17, 2019

(65) Prior Publication Data
US 2019/0307406 A1 Oct. 10, 2019

Related U.S. Application Data

(62) Division of application No. 14/688,751, filed on Apr. 16, 2015.
(Continued)

(51) Int. Cl.
*A61B 6/10* (2006.01)
*A61N 5/10* (2006.01)
(Continued)

(52) U.S. Cl.
CPC ............ *A61B 6/107* (2013.01); *A61B 6/0407* (2013.01); *A61N 5/1081* (2013.01); *G21F 3/00* (2013.01);
(Continued)

(58) Field of Classification Search
CPC ......... A61B 6/0407; A61B 6/107; G21F 3/00; A61N 5/1081; A61N 2005/1061; A61N 2005/1094
See application file for complete search history.

(56) References Cited

U.S. PATENT DOCUMENTS 5,646,971 A * 7/1997 Howe ................... G21C 19/06
376/272
6,512,813 B1 * 1/2003 Krispel ................ A61N 5/1042
378/64
(Continued)

FOREIGN PATENT DOCUMENTS

WO 2015/161036 10/2015

OTHER PUBLICATIONS https://hautevitrine.com/tag/nuclear-shelter/, Mar. 15, 2012, Leslie Hossack.*
(Continued)

*Primary Examiner* — Bo Joseph Peng
(74) *Attorney, Agent, or Firm* — DLA Piper LLP (US)

(57) ABSTRACT

Radiation therapy systems and their components, including secondary radiation shields. At least some versions of the disclosed systems combine a radiation delivery device, a primary radiation shielding device, and a secondary shielding layer into an integrated, modular unit. This is accomplished by using a small direct beam shield capable of blocking a primary beam from a radiation delivery device. In turn, a thinner shielding layer can be used to surround the radiation delivery device and primary shielding device, enabling a single modular unit to be delivered to an installation site. In some embodiments, a bed may be disposed within the secondary shielding layer. In some embodiments,
(Continued)

the system is configured to provide up to 4-pi (4π) steradians of radiation coverage to the bed from the radiation delivery device.

20 Claims, 20 Drawing Sheets

Related U.S. Application Data

(60) Provisional application No. 61/980,559, filed on Apr. 16, 2014.

(51) Int. Cl.
  *A61B 6/04* (2006.01)
  *G21F 3/00* (2006.01)

(52) U.S. Cl.
  CPC ............... *A61N 2005/1061* (2013.01); *A61N 2005/1094* (2013.01)

(56) References Cited

U.S. PATENT DOCUMENTS

| | | | |
|---|---|---|---|
| 7,014,361 | B1 | 3/2006 | Ein-Gal |
| 7,526,066 | B2 | 4/2009 | Koshnitsky et al. |
| 7,648,273 | B2 | 1/2010 | Manzke et al. |
| 7,679,073 | B2* | 3/2010 | Urano .................... A61N 5/10 250/492.3 |
| 7,728,311 | B2 | 6/2010 | Gall |
| 7,758,241 | B2 | 7/2010 | Sliski et al. |
| 7,847,275 | B2 | 12/2010 | Lifshitz et al. |
| 2004/0005027 | A1* | 1/2004 | Nafstadius ........... A61N 5/1049 378/65 |
| 2008/0203331 | A1 | 8/2008 | Murphy |
| 2008/0245978 | A1* | 10/2008 | Yanke .................... F42B 39/14 250/515.1 |
| 2012/0150016 | A1 | 6/2012 | Rathee et al. |
| 2012/0150018 | A1 | 6/2012 | Yamaya et al. |
| 2012/0294424 | A1 | 11/2012 | Chin et al. |
| 2013/0144104 | A1 | 6/2013 | Adler et al. |
| 2014/0171725 | A1 | 6/2014 | Adler |
| 2016/0095558 | A1 | 4/2016 | Choy et al. |

OTHER PUBLICATIONS

Meeting Room in Pumpkin Shape Construction, http://www.marvelbuilding.com/meeting-room-pumpkin-shape-construction-pumpkin-room.html, Sep. 2012.*

Chui, The power of proton therapy, symmetry magazine, Dec. 1, 2008.*

Department of Veterans Affairs, "Radiation Therapy Service Design Guide", Apr. 2008, 63 pages.

Heeswijk, "Room with a view (Positioning)", Jeanneworks, Typologies & Capacities, http://www.jeanneworks.net/projects/room_with_a_view_positioning/, Jan. 1995, 2 pages.

Marvelbuilding, "Meeting Room in Pumpkin Shape Construction—Pumpkin Room", http://www.marvelbuilding.com/meeting-room-pumpkin-shape-construction-pumpkin-room.html, printed Jun. 4, 2019, 4 pages.

Chui, "The power of proton therapy", Symmetry: dimensions of particle physics, https://www.symmetrymagazine.org/article/december-2008/the-power-of-proton-therapy, Dec. 1, 2008, 16 pages.

International Search Report and Written Opinion issued in PCT/US2015/026108, dated Sep. 16, 2015, 12 pages.

Non Final Office Action issued in U.S. Appl. No. 14/688,751, dated Nov. 1, 2018, 14 pages.

* cited by examiner

RADIATION THERAPY SYSTEMS THAT INCLUDE PRIMARY RADIATION SHIELDING, AND MODULAR SECONDARY RADIATION SHIELDS

CROSS-REFERENCE TO RELATED APPLICATIONS

This is a divisional of U.S. patent application Ser. No. 14/688,751, filed Apr. 16, 2015, which claims priority to U.S. Provisional Application Ser. No. 61/980,559, filed on Apr. 16, 2014, the contents of which are herein incorporated by reference in its entirety.

BACKGROUND

1. Field of the Invention

The disclosed invention relates generally to radiation therapy systems, such as linear accelerator (linac) systems, and to radiation shields for use with such systems.

2. Description of Related Art

A typical example of a radiation therapy photon producing linac system comprises a linac device placed within a large, thick, concrete-lined room or bunker. The linac usually rotates on a horizontal axis around a patient lying on a horizontal platform. Primary radiation is generated from the head of the linac. Primary radiation can emanate in multiple directions and potentially has considerable penetrating power depending on the energy range of the linac. Secondary radiation arises when primary radiation interacts with components of the linac, the patient, equipment in the bunker, and/or the walls of the bunker. Secondary radiation typically has less penetrating power, but remains an exposure health risk.

The primary radiation beam is collimated to be mostly unidirectional. As the patient is treated, much of the primary radiation beam exits the patient and hits the thick walls of the bunker. The bunker is intended to shield the staff and the public from both primary radiation and secondary radiation. The bunker's shielding walls are stationary and completely decoupled from the linac device itself. Some such systems have a shield, or beam stopper, opposing the radiation source and that stays aligned with (and in opposition to) the radiation source as the two rotate. Configurations of linac systems may be limited in their directional geometry by their inherent size, orientation of beams relative to the patient, and integrated devices used in the control and guidance of the linac beam. Examples of radiation therapy systems are disclosed in U.S. Pat. Nos. 6,512,813 and 7,758,241; and in Pub. Nos. US 2012/0150016; US 2012/0150018; US 2012/0294424; and US 2013/0144104.

SUMMARY

This disclosure includes embodiments of radiation therapy systems in combinations with shielding for both primary and secondary radiation. This disclosure also includes embodiments of components of such systems, such as rail devices (or rail structures) to which one or more radiation sources and, optionally, one or more imaging sources may be coupled; such components may also include a housing for covering at least a portion of such rail devices. This disclosure also includes embodiments of shields, including shields having a dome shape and including a pivotable door that can cover an opening through which a patient may enter the shield.

Some embodiments of the disclosed systems comprise a radiation therapy apparatus that includes an inner layer having a radiation delivery device and a primary radiation shielding device; and an outer layer having a secondary radiation shielding device.

In some embodiments, the outer layer comprises a dome shape. In some embodiments, the inner layer further comprises one or more rails mounted on an inner surface of the inner layer, the rails being disposed in a circular shape. In some embodiments, the radiation delivery device and the primary radiation shielding device are disposed on the one or more rails, the primary radiation shielding device disposed opposite the radiation delivery device and configured to block primary radiation emitted from the radiation delivery device. In some embodiments, the apparatus further comprises a treatment table disposed inside the one or more rails. In some embodiments, the treatment table comprises a platform supported by one or more legs connected to the inner surface of the inner layer. In some embodiments, the treatment table is configured to isocentrically rotate 360 degrees around a vertical axis. In some embodiments, the treatment table is configured to move in a lengthwise direction, a widthwise direction, and an orthogonal direction relative to a horizontal axis, thereby allowing up to 4-pi ($4\pi$) steradians of beam entry toward the patient.

In some embodiments, the inner layer further comprises one or more imaging sources. In some embodiments, the one or more imaging sources are disposed on the one or more rails. In some embodiments, the inner layer further comprises one or more imaging panels. In some embodiments, the one or more imaging sources are disposed on the one or more rails, the one or more imaging panels disposed opposite the one or more imaging sources and configured to receive radiation emitted from the one or more imaging sources. In some embodiments, the one or more imaging sources are X-ray emitting devices. In some embodiments, the one or more imaging sources provide one or more of 2D images, 3D images, 2D plus time images, and 3D plus time images.

In some embodiments, the radiation delivery device comprises one or more of a linac device or a Co-60 emitting device. In some embodiments, the primary radiation shielding device comprises a beam block. In some embodiments, the radiation delivery device and the primary radiation shielding device rotate around a horizontal axis in synchrony with each other. In some embodiments, the radiation delivery device and the primary radiation shielding device rotate around a vertical axis in synchrony with each other.

Some embodiments of the disclosed systems comprise a radiation therapy apparatus that includes an inner layer having a radiation delivery device and a primary radiation shielding device; and an outer layer having a secondary radiation shielding device, where the inner layer is movable in relation to the outer layer and the outer layer is disposed in a cylindrical tube shape.

In some embodiments, the inner layer further comprises one or more rails mounted on an inner surface of the inner layer, the rails being disposed in a circular shape around a horizontal axis. In some embodiments, the radiation delivery device and the primary radiation shielding device are disposed on the one or more rails, the primary radiation shielding device disposed opposite the radiation delivery device and configured to receive primary radiation emitted from the radiation delivery device. In some embodiments, the radiation delivery device and the primary radiation shielding device rotate around a horizontal axis in synchrony with each other. In some embodiments, the radiation delivery device further comprises a treatment table disposed inside the one or more rails. In some embodiments, the treatment table is movable and configured to slide in a longitudinal direction along the horizontal axis. In some embodiments, the one or more rails are disposed to slide in a longitudinal direction along the horizontal axis. In some embodiments, the outer layer covering the ends of the tube comprises doors, the doors configured to enable the treatment table to enter the tube through a first door and exit the tube through a second door.

Some embodiments of the disclosed systems comprise a radiation therapy apparatus, comprising a radiation delivery device disposed to rotate around a horizontal axis; a primary radiation shielding device; and an outer layer comprising a secondary radiation shielding device, configured to cover the radiation delivery device.

In some embodiments, the outer layer comprises a dome shape. In some embodiments, the radiation delivery device further comprises one or more rails mounted on an inner surface of the outer layer, the rails being disposed in a circular shape. In some embodiments, the primary radiation shielding device is disposed on the one or more rails, the primary radiation shielding device disposed opposite the radiation delivery device and configured to block primary radiation emitted from the radiation delivery device. In some embodiments, the radiation delivery device comprises one or more of a linac device or a Co-60 emitting device. In some embodiments, the primary radiation shielding device comprises a beam block. In some embodiments, the radiation delivery device and the primary radiation shielding device rotate around a horizontal axis in synchrony with each other.

In some embodiments, the radiation therapy apparatus comprises a secondary shielding device comprising a cylinder-shaped portion and a ring-shaped portion. In some embodiments, the ring-shaped portion is disposed to cover a radiation delivery device, and a primary radiation shielding device. In some embodiments, a housing is configured to cover the secondary shielding device.

In some embodiments, the radiation therapy apparatus comprises one or more rails disposed in a circular shape and configured to rotate around a horizontal axis. In some embodiments, the radiation delivery device and the primary radiation shielding device are coupled to the one or more rails, the primary radiation shielding device being disposed opposite the radiation delivery device and configured to receive primary radiation emitted from the radiation delivery device. In some embodiments, the apparatus is configured so that the radiation delivery device and the primary radiation shielding device can rotate around a horizontal axis in synchrony with each other.

In some embodiments, the apparatus further comprises a treatment table disposed inside the one or more rails. In some embodiments, the treatment table is movable and configured to slide in a longitudinal direction inside the inner layer. In some embodiments, the housing comprises one or more doors coupled to the third cylinder-shaped section.

In some embodiments, a radiation therapy apparatus further comprises a gear device. In some embodiments, a rotating member is coupled to the gear device, the rotating member configured to rotate around a vertical axis. In some embodiments, the inner layer comprises a ring structure coupled to the rotating member. In some embodiments, the ring structure rotates around the vertical axis.

In some embodiments, the apparatus further comprises a treatment table disposed inside the ring structure. In some embodiments, the treatment table is supported by one or more legs coupled to the outer layer. In some embodiments, the apparatus further comprises a floor, the floor being coupled to the ring structure and configured to rotate around a vertical axis. In some embodiments, the floor further comprises one or more openings disposed around the one or more legs, the openings configured to enable the floor to avoid contact with the one or more legs when the floor rotates about the vertical axis.

In some embodiments, the apparatus is configured so that the radiation delivery device and the primary radiation shielding device can rotate around a horizontal axis in synchrony with each other. In some embodiments, the apparatus is configured to provide $4\pi$ steradians of radiation coverage to the isocentrically rotating treatment table.

In some embodiments, a method of manufacturing a radiation therapy device comprises disposing a radiation delivery device on an inner layer; disposing a primary radiation shielding device on an inner layer, where the primary radiation shielding device is configured to block a primary radiation beam emitted from the radiation delivery device; and disposing an outer layer covering the inner layer, the outer layer comprising a secondary radiation shielding layer configured to block secondary radiation.

In some embodiments, a radiation therapy apparatus comprises a circular rail structure comprising a radiation delivery device and a primary radiation shielding device. In some embodiments, the rail structure is disposed to rotate around a horizontal axis. In some embodiments, a bed is configured to isocentrically rotate 360 degrees around a vertical axis and is disposed at a center of the circular rail structure. In some embodiments, a secondary radiation shielding device is configured to cover the radiation delivery device and the primary radiation shielding device. In some embodiments, the bed is further configured to move in a vertical direction and configured to receive $4\pi$ steradians of radiation coverage.

In some embodiments, a radiation therapy apparatus comprises a circular rail structure comprising a radiation delivery device and a primary radiation shielding device. In some embodiments, the rail structure is disposed to rotate around a horizontal axis. In some embodiments, a bed is configured to move in three spatial directions and is disposed at a center of the circular rail structure. In some embodiments, a secondary radiation shielding device is configured to cover the radiation delivery device and the primary radiation shielding device. In some embodiments, the bed is further configured to move in directions that comprise length, width, and depth and receive $4\pi$ steradians of radiation coverage.

The term "coupled" is defined as connected, although not necessarily directly, and not necessarily mechanically. Two items are "couplable" if they can be coupled to each other. Unless the context explicitly requires otherwise, items that are couplable are also decouplable, and vice-versa. One non-limiting way in which a first structure is couplable to a second structure is for the first structure to be configured to be coupled (or configured to be couplable) to the second structure. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a systems, or a component of a systems, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first" and "second" are used only to differentiate structures or features, and not to limit the different structures or features to a particular order.

Any embodiment of any of the disclosed systems or system components (such as shields) can consist of or consist essentially of—rather than comprise/include/contain/have—any of the described elements and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures illustrate at least one of the described elements using a graphical symbol that will be understood by those of ordinary skill in the art.

DESCRIPTION OF ILLUSTRATIVE EMBODIMENTS

Figure 1:
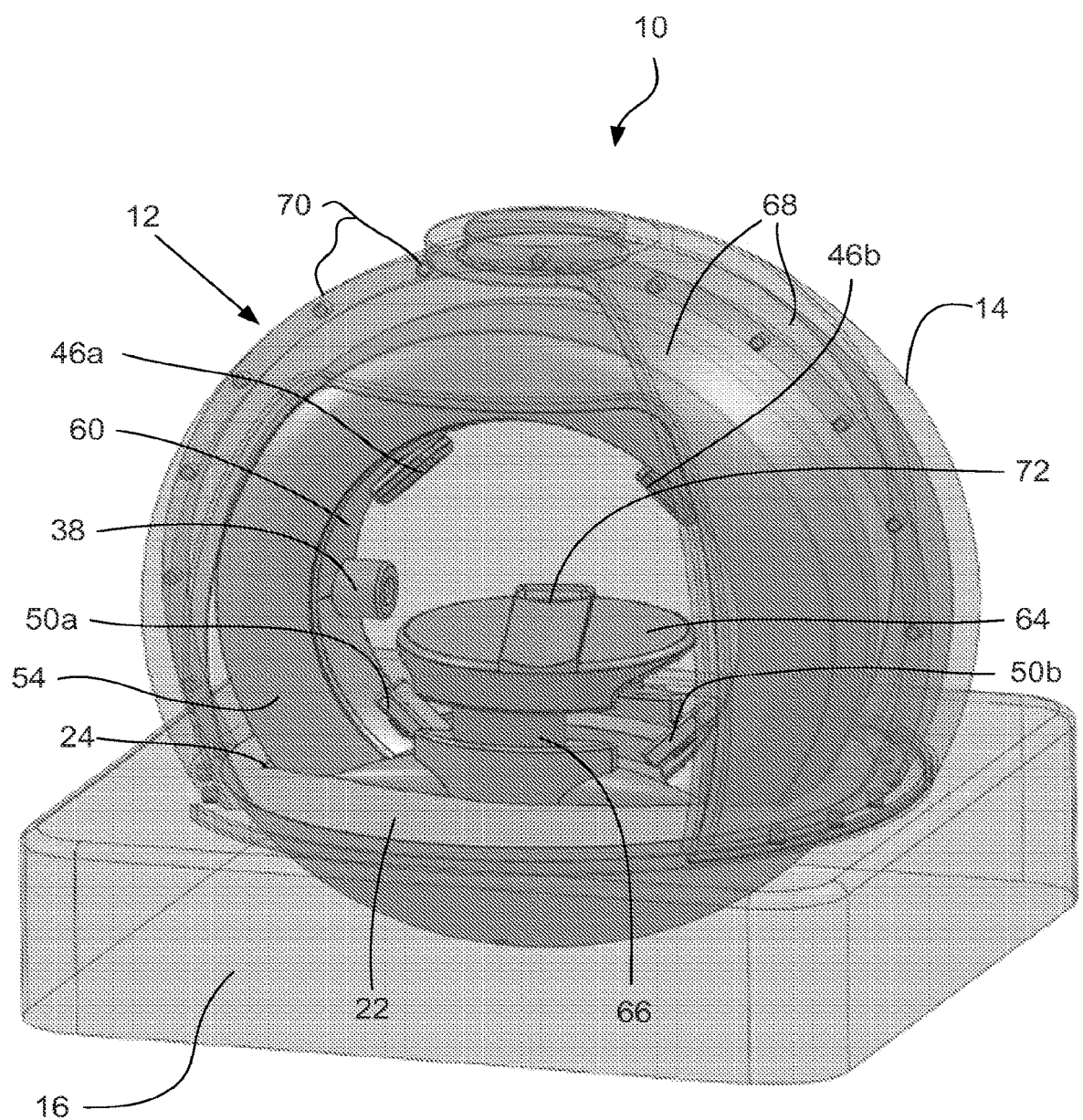
FIG. 1 depicts a perspective view of an embodiment of one of the disclosed radiation therapy systems.

Referring now to the drawings, and more particularly to FIG. 1, system 10, which is one embodiment of the disclosed systems, is shown. In the embodiment shown, a modular dome 12, door 14, and base 16 comprise an outer shielding layer for a radiation therapy device. Floor 22 may be disposed inside base 16. In the embodiment shown, dome 12 is comprised of two sections 68 coupled together with fasteners 70. In other alternative embodiments, dome 12 may comprise a single section or more than two sections coupled together, and may be characterized as a stationary element. Sections 68 may be coupled together such as by riveting, bolting, welding, bonding, brazing, dimpling, or the like. In the embodiment shown, ring 54 is disposed within dome 12. Inner face 60 may be configured to rotate about a horizontal axis. This rotation enables collimator 38, a primary shielding device (not shown), imaging sources 46a-b, and imaging panels 50a-b to be positioned in various configurations about treatment table 64. In the embodiment shown, treatment table 64 is disposed around an isocenter of ring 54 and comprises bed 72 disposed centrally on treatment table 64. The isocenter of ring 54 represents the point in space where radiation beams emitted from collimator 38 intersect as inner face 60 rotates. Treatment table 64 may rotate about a vertical axis via tracks, rollers, ball bearings, or the like. In the embodiment shown, treatment table 64 further comprises one or more legs 66 coupling treatment table to the center of floor 22. One or more legs 66 may be disposed on a side of channel 24. In some embodiments, legs 66 may be configured to move or telescope in a vertical direction. In the embodiment shown, treatment table 64 is disposed over channel 24 and is configured with adequate height to allow collimator 38, imaging sources 46a-b, and imaging panels 50a-b, protruding from (or otherwise having portions positioned more inwardly than) inner face 60 to clear the underside of treatment table 64. In some embodiments, treatment table 64 may move up and down in a vertical direction via legs 66. In the embodiment shown, ring 54 is disposed to provide a source-to-isocenter distance of greater than 1 meter (m) between a radiation source (not shown) and the isocenter.

Figure 2A:
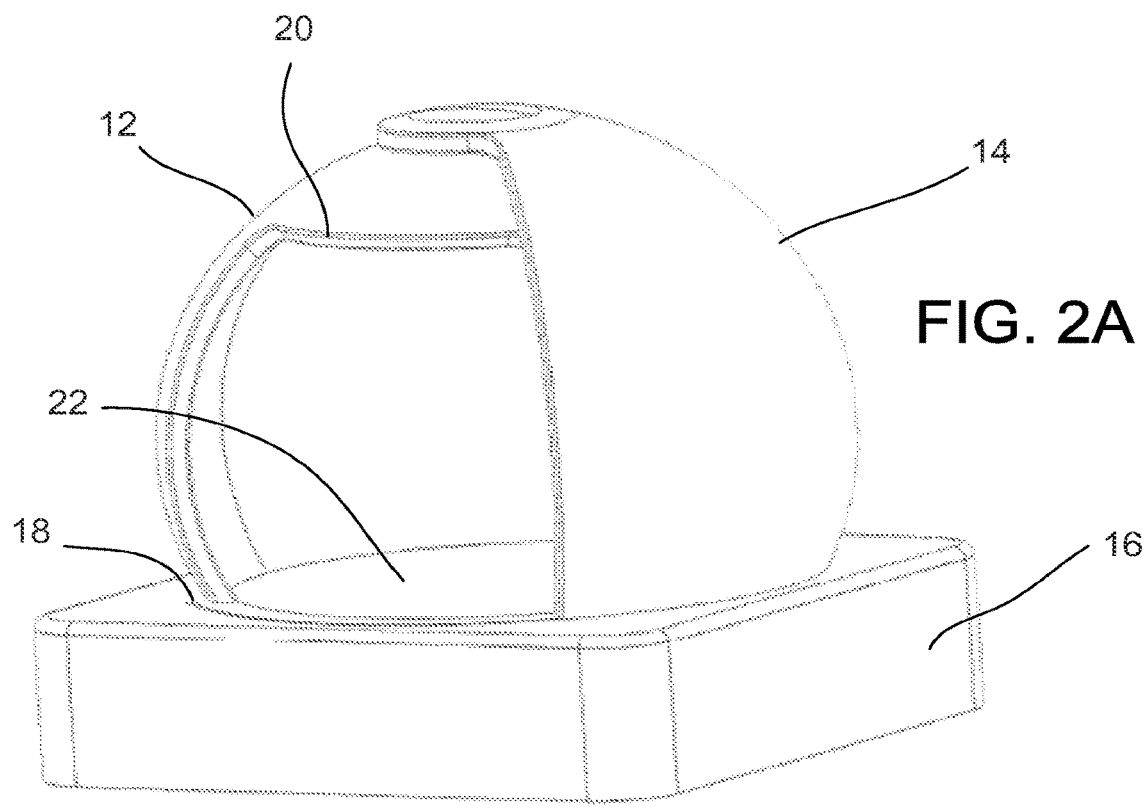
FIGS. 2A and 2B depict perspective and top views, respectively, of an embodiment of a secondary shielding layer of the system of FIG. 1.
Figure 2B:
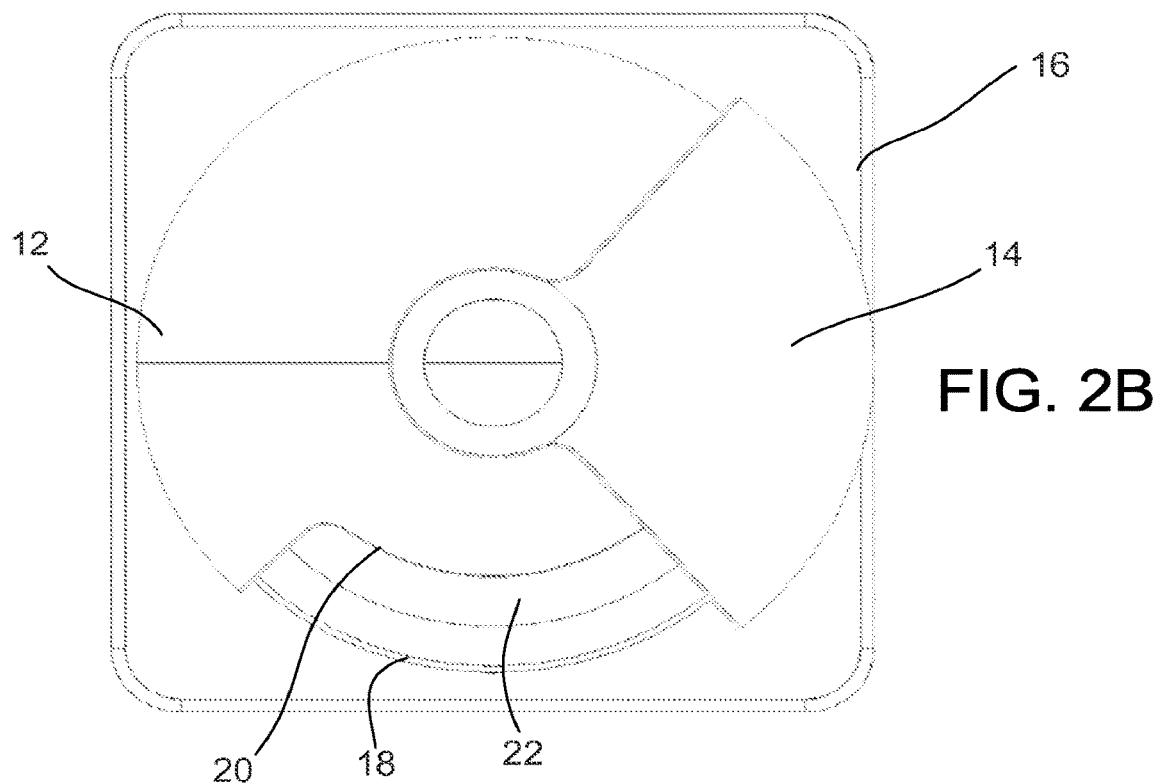

FIGS. 2A and 2B show an embodiment of the disclosed shields, which can be retrofitted to an existing radiation therapy system or used with one of the disclosed radiation therapy systems. Dome 12 can be coupled to base 16 such as by riveting, bolting, welding, bonding, or the like. Door 14 can be coupled to the top of dome 12 in such a way as to allow door 14 to rotate around dome 12 on a vertical axis. Door 14, as the depicted embodiment shows, may have a curved surface or profile that matches or cooperates with an adjacent surface or profile of dome 12. Accordingly, dome 12 and door 14 may, together, have a substantially dome configuration.

In the embodiment shown, door 14 is disposed on the outside of dome 12 and enabled to partially rotate around dome 12. In other embodiments, door 14 may be disposed on the inside of dome 12 and/or may be enabled to completely rotate around dome 12. The bottom of door 14 can be disposed in guide 18. Guide 18 may be set into base 16 and outside a side face of dome 12 in an arc shape. Alternatively, guide 18 may be disposed on top of base 16. Door 14 may slide along guide 18 using tracks, rollers, ball bearings, or the like.

Dome 12 may be configured with an opening. In the embodiment shown, opening 20 is disposed in a face of dome 12. Opening 20 is sufficiently large to admit one or more humans to the interior of dome 12. In the embodiment shown, door 14 is disposed to cover and uncover opening 20 by rotating around dome 12 along the path of guide 18. In the embodiment shown, floor 22 is disposed over the bottom of dome 12. The top of floor 22 may be on the same horizontal plane as the top of base 16. Alternatively, floor 22 may be on a different horizontal plane than the top of base 16.

In the embodiment shown, the outer layer of the depicted system—including dome 12, door 14, and base 16—is constructed of a single type or multiple types of radiation shielding material such as lead, steel, tungsten, concrete, or the like. In the embodiment shown, the thicknesses of dome 12, door 14, and base 16 are sufficient to block secondary radiation. For purposes of description, primary radiation comprises radiation emitting directly from a radiation delivery device passing through the opening of collimator 38. Secondary radiation comprises all other radiation present, such as radiation emitted from the radiation delivery device in other than the intended therapeutic direction, radiation scattered within a patient, or radiation scattered within a treatment room.

Figure 3:
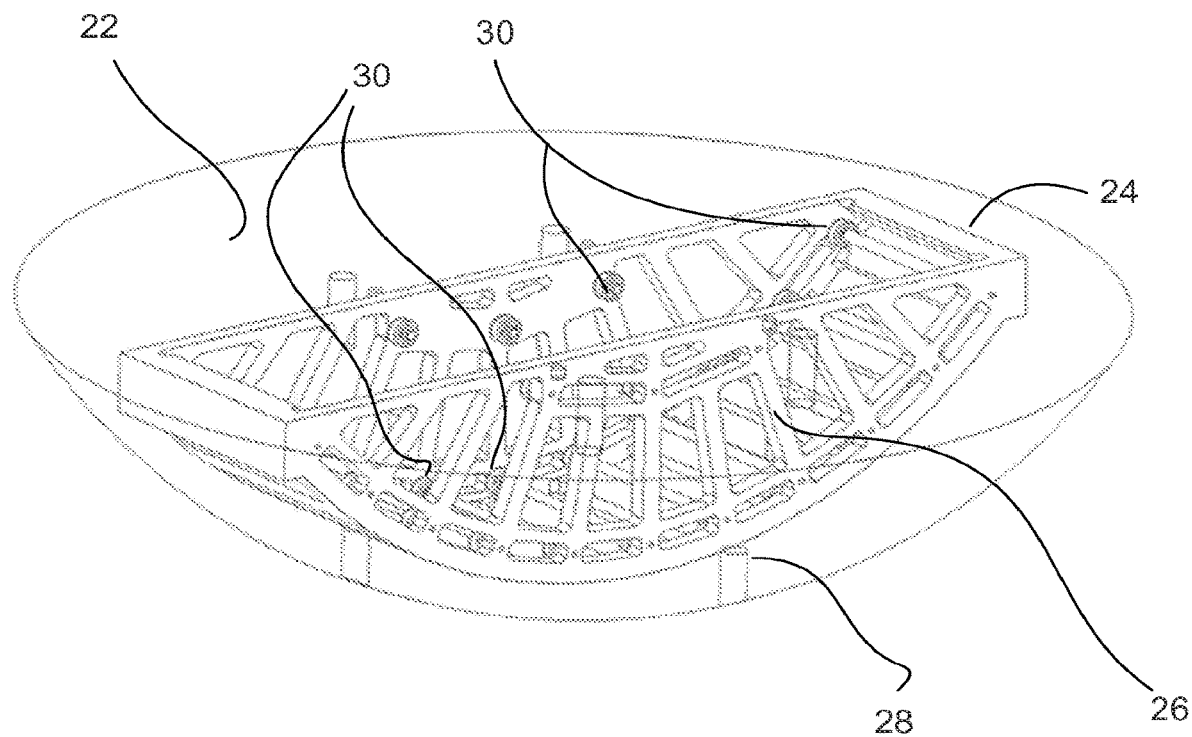
FIG. 3 depicts a perspective, cross-sectional view of a floor section of the secondary shielding layer of FIGS. 2A and 2B.

As shown in FIG. 3, floor 22 may be disposed to cover the bottom of dome 12. Floor 22 may comprise a covering over open space between the top surface of the bottom of dome 12 and the bottom surface of floor 22. Alternatively, floor 22 may comprise a solid material coupled to the bottom of dome 12 and filling in the bottom of dome 12.

FIG. 3 also shows an embodiment of another component of the disclosed systems—a channel that supports a rotating rail structure to which the radiation delivery device and, optionally, one or more imaging sources may be coupled. In the embodiment shown, channel 24 is inset into floor 22 and positioned such that a plane located at and parallel to the top of surface of channel 24 is coincident with a plane positioned on the surface of floor 22. Alternatively, the top of channel 24 may be positioned above or below the surface of floor 22. In the embodiment shown, the bottom surface of channel 24 is an arc shape, which in some embodiments can mirror or match the arc shape of dome 12. Channel 24 also includes a structural framework 26 that spans the sides and bottom surface of channel 24. Channel 24 may be supported in the system by being coupled to base 16, such as by legs 28, which may be coupled to floor 22. Channel 24 may comprise rolling mechanisms 30 disposed intermittently along the inside surface (such as along both the sides and bottom) of framework 26, which mechanisms will facilitate the movement of the rail structure described below. Rolling mechanisms 30 can be tracks, rollers, ball bearings, or the like. In an alternative embodiment, channel 24 may be solid, and may not include framework 26.

Figure 4:
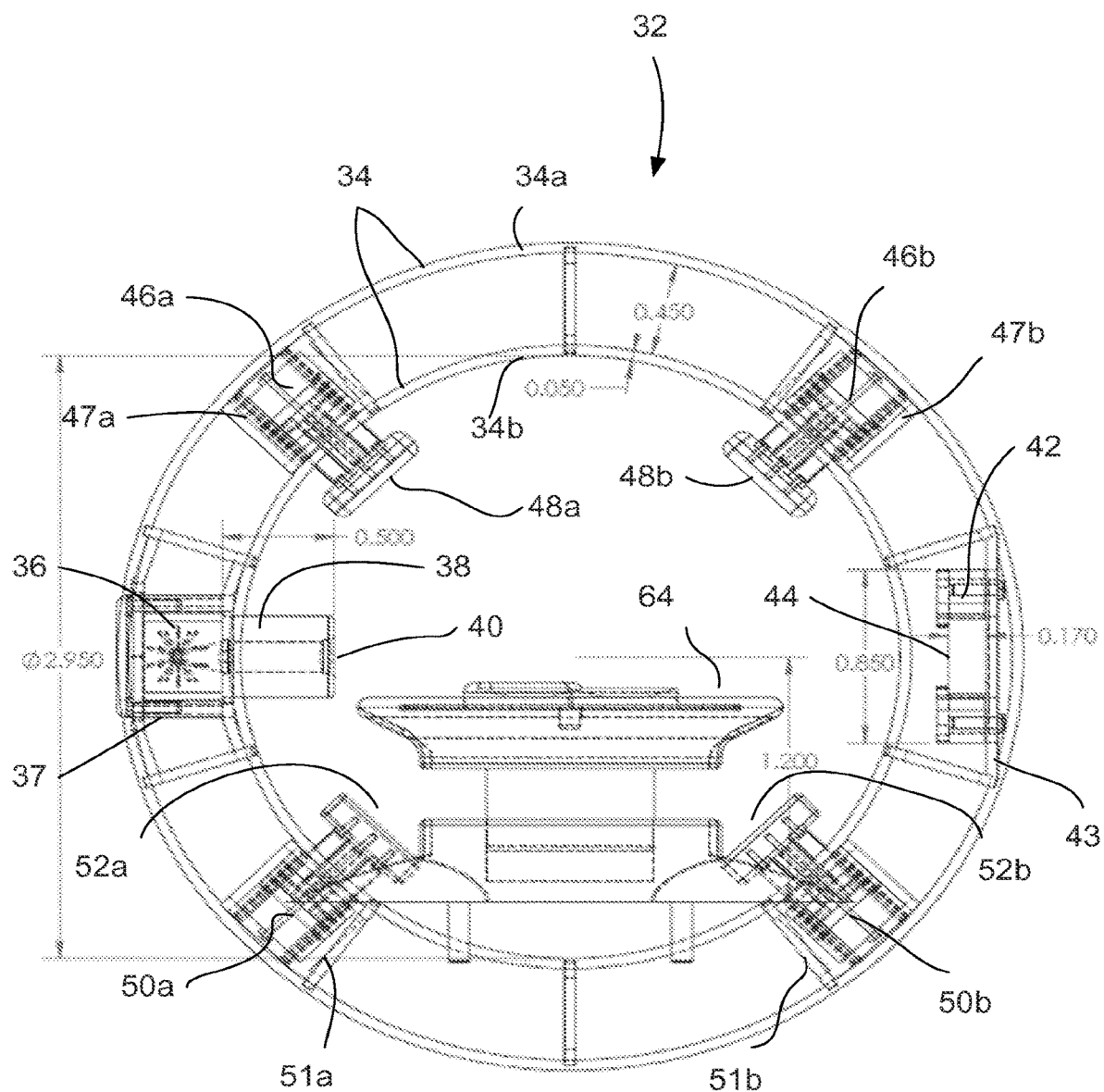
FIG. 4 depicts a side view of a rail structure disposed inside the secondary shielding layer of the system of FIG. 1.

FIG. 4 shows an embodiment of another component of the disclosed systems—a rotating rail structure to which the radiation delivery device and, optionally, one or more imaging sources may be coupled. In the embodiment shown in FIG. 4, rail structure 32 comprises one or more rails 34 disposed in a circular shape. In the embodiment shown, rails 34 are 0.050 m thick and have 0.45 m of distance between an outer rail 34a and inner rail 34b. In the embodiment shown, a diameter of rail structure 32 is 3.4 m and an inner diameter is 2.95 m. In other embodiments involving the depicted structures, other dimensions may be used.

In the embodiment shown, radiation delivery device 36 and collimator 38 are provided. Radiation delivery device 36 may comprise a linac, proton or ion beam accelerator, Co-60 isotopic source, ortho- or supervoltage X-ray generator, or other particle accelerator.

Radiation delivery device 36 may be coupled to one or more rails 34 in a stationary position. Alternatively, radiation delivery device 36 may be coupled to one or more rails 34 so as to allow radiation delivery device to move along rail structure 32. In the embodiment shown, radiation delivery device 36 is affixed to receptacle 37, which is coupled to rail structure 32. In the embodiment shown, radiation delivery device 36 further comprises collimator 38. Alternatively, radiation delivery device 36 may be provided without collimator 38. In the embodiment shown, collimator 38 is positioned to have emission face 40 directed toward the inner area and center of rail structure 32. In the embodiment shown, collimator 38 is 0.500 m long. In other embodiments involving the depicted structures, other dimensions may be used.

In the embodiment shown, primary shielding device 42 is provided. Primary shielding device 42 may be a beam block and may be comprised of lead, steel, tungsten, concrete, or other suitable shielding material. In the embodiment shown, the thickness of primary shielding device 42 is sufficient to block a primary radiation beam of radiation delivery device 36 without additional assistance. Primary shielding device 42 may be configured to block radiation so that it reduces at least 99.9% of the radiation resulting from the operation of radiation delivery device 36.

Primary shielding device 42 may be coupled to one or more rails 34 in a stationary position. Alternatively, primary shielding device 42 may be coupled to one or more rails 34 so as to allow primary shielding device 42 to move along rail structure 32. In the embodiment shown, primary shielding device 42 is affixed to receptacle 43, which is coupled to rail structure 32. In the embodiment shown, primary shielding device 42 is positioned to have receiving face 44 directed toward the inner area and center of rail structure. In the embodiment shown, primary shielding device 42 is positioned opposite radiation delivery device 36 on rail structure 32. In some embodiments, an opposite position comprises being positioned at a 180° angle from another position. By positioning primary shielding device 42 opposite radiation delivery device 36, primary shielding device 42 directly receives and blocks primary radiation emitted by radiation shielding device 36. In the embodiment shown, primary shielding device 42 is 0.850 m wide and 0.170 m thick. In other embodiments involving the depicted structures, other dimensions may be used.

In the embodiment shown, one or more imaging sources 46a, 46b are provided. Imaging sources 46a-b may comprise X-ray, cone beam computed tomography (CT), ultrasound imaging, positron emission tomography (PET), single photon emission computed tomography (SPECT), or magnetic resonance imaging (MRI) technologies.

Imaging sources 46a-b may be coupled to one or more rails 34 in a stationary position. Alternatively, imaging sources may be coupled to one or more rails 34 so as to allow imaging sources 46 to move along rail structure 32. In the embodiment shown, imaging sources 46a-b are affixed to receptacles 47a-b, respectively, which are coupled to rail structure 32. In the embodiment shown, imaging sources 46a-b are positioned to have emission faces 48a-b directed toward the inner area and center of rail structure 32. Imaging sources 46a-b may be provided intermittently on rail structure 32 between radiation delivery device 36 and primary shielding device 42.

In the embodiment shown, one or more imaging panels 50a-b are provided. Imaging panels 50a-b may receive the emission of X-rays or the like from imaging sources 46a-b. Imaging panels 50a-b may be coupled to one or more rails 34 in a stationary position. Alternatively, imaging panels 50a-b may be coupled to one or more rails 34 so as to allow imaging panels 50a-b to move along rail structure 32. In the embodiment shown, imaging panels 50a-b are affixed to receptacles 51a-b, respectively, which are coupled to rail structure 32. In the embodiment shown, imaging panels 50a-b are positioned to have receiving faces 52a-b directed toward the inner area and center of rail structure 32. Imaging panels 50a-b may be provided intermittently on rail structure 32 between radiation delivery device 36 and primary shielding device 42. In the embodiment shown, imaging panels 50a-b are positioned opposite imaging sources 46a-b on rail structure 32. By positioning imaging panels 50a-b opposite imaging sources 46a-b, imaging panels 50a-b directly receive imaging radiation emitted by imaging sources 46a-b.

Figure 5:
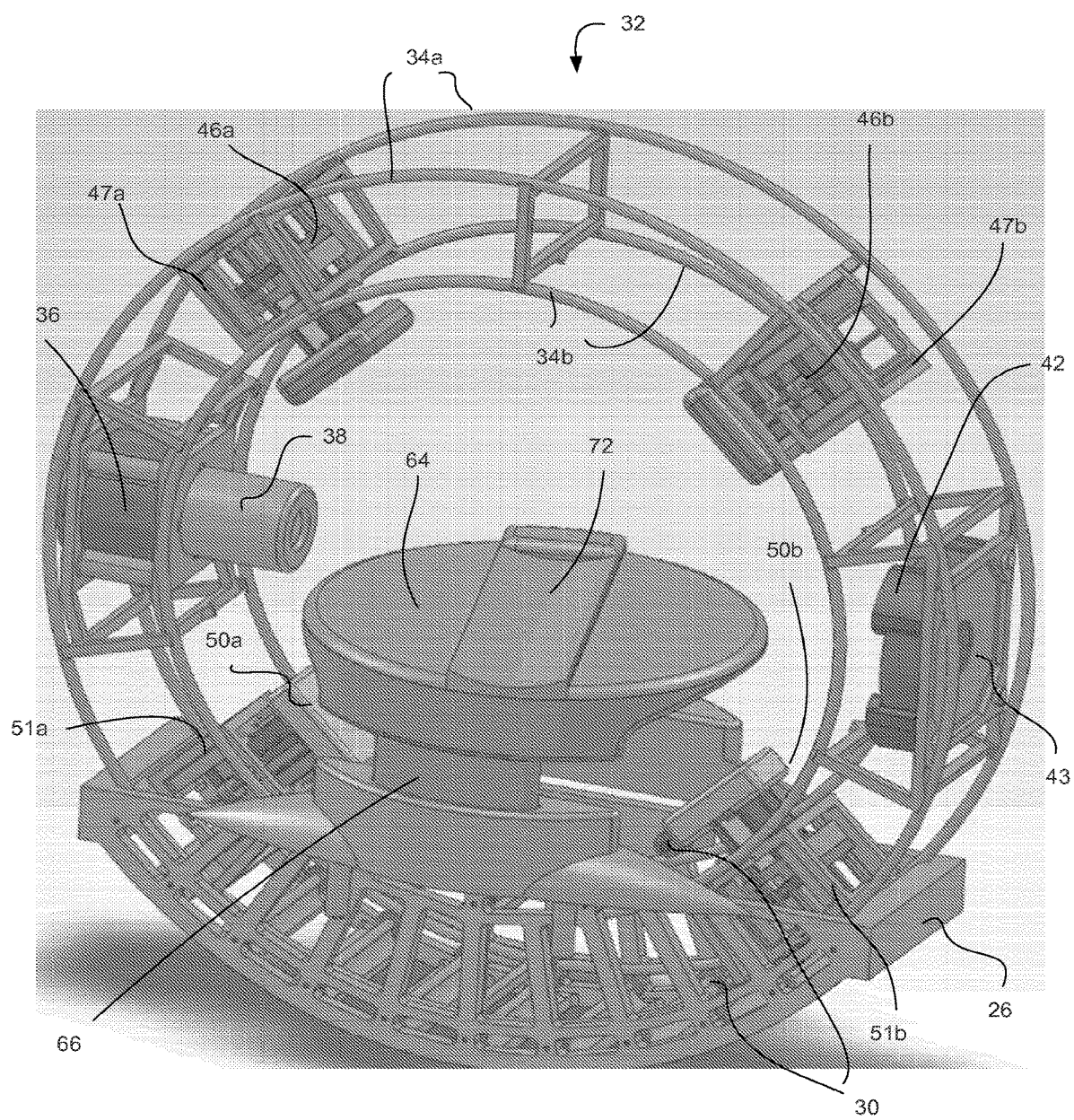
FIG. 5 depicts a perspective view of a combination of the rail structure of FIG. 4 with a treatment table and a framework of the system of FIG. 1.

FIG. 5 shows rail structure 32 in operative relation with framework 26, and further shows an embodiment of another component of some of the disclosed systems—treatment table 64. In the embodiment shown in FIG. 5, rail structure 32 is combined with framework 26 and treatment table 64. Rail structure 32 is configured to be set into framework 26 and slide along rolling mechanisms 30. In the embodiment shown, outer rails 34a of rail structure 32 are disposed on a top surface of rolling mechanisms 30 disposed on the bottom of framework 26. In the embodiment shown, inner rails 34b are disposed on a bottom surface of rolling mechanisms 30 disposed on the sides of framework 26 in an arc shape. Rolling mechanisms 30 may be coupled to one or more electric power sources such as an electric motor, which may be configured to power the rotation of rolling mechanism 30. In the embodiment shown, as rolling mechanisms 30 rotate, outer rails 34a and inner rails 34b are moved along rolling mechanisms 30. This action rotates rail structure 32 around treatment table 64. Although not shown, braking mechanisms may also be coupled to framework 26 for applying to one or both of the outer and inner rails in order to stop the motion of the rails as desired. In the embodiment shown, collimator 38, imaging sources 46a-b, and imaging panels 50a-b, are disposed to rotate around treatment table 64 as rail structure 32 rotates. Collimator 38, imaging sources 46a-b, and imaging training table 64 as rail structure 32 rotates.

Figure 6A:
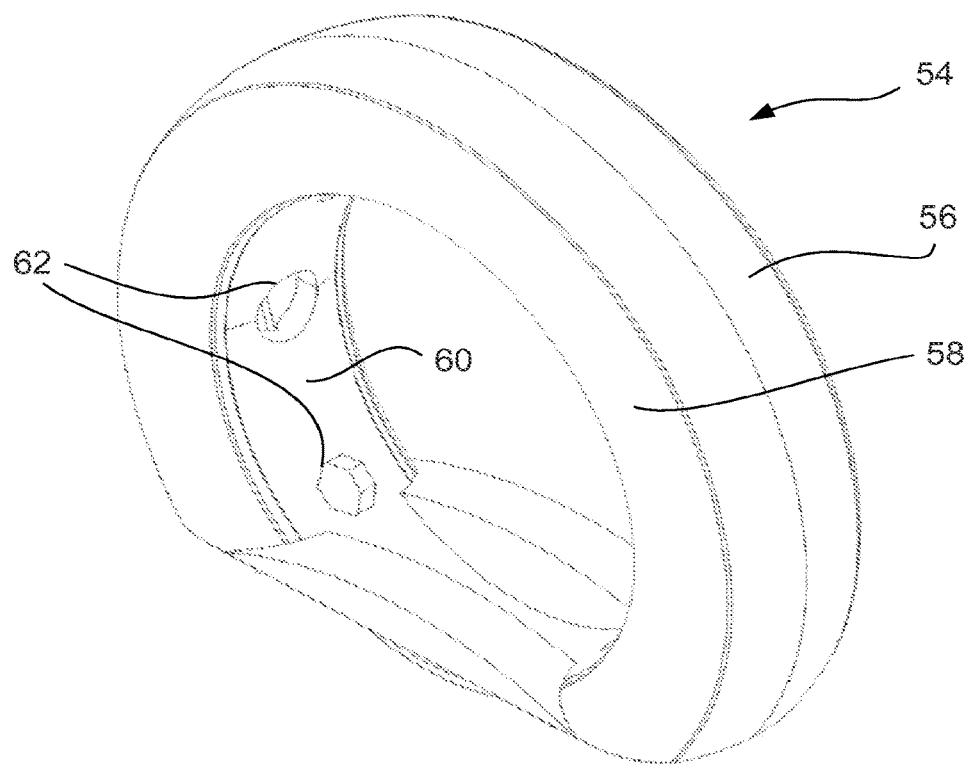
FIGS. 6A and 6B depict perspective and top views of a ring of the system of FIG. 1.
Figure 6B:
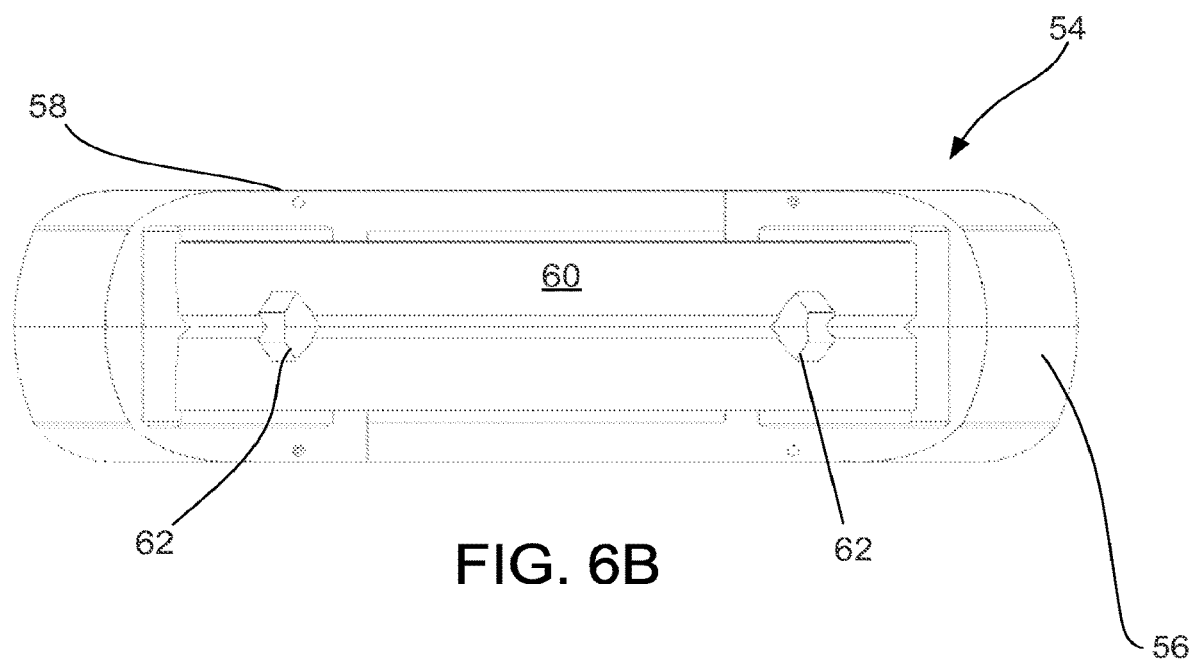

FIGS. 6A and 6B show an embodiment of another component of the disclosed systems—a housing for the rotating rail structure to which the radiation delivery device and, optionally, one or more imaging sources may be coupled. In the embodiment shown in FIGS. 6A and 6B, the outer housing, which is depicted as ring 54, comprises outer face 56, side faces 58, and inner face 60. Inner face 60 comprises openings or holes 62 disposed at intermittent intervals along the surface of inner face 60, which openings are configured to allow through-placement of portions of the relevant radiation source(s), imaging source(s), and their respective shields/panels. The portions of ring 54 other than inner face 60 may comprise two halves or other multiple modular pieces coupled together, with each half or piece including a portion of outer face 56 and a side face 58. In the embodiment shown, the outer and side faces of ring 54 are stationary and are coupled to floor 22 in any suitable manner. Inner face 60 may be coupled to rail structure 32 so as to rotate with rail structure 32 around a horizontal axis; thus, inner face 60 may be movable relative to the outer and side faces of ring 54 and may also be movable through channel 24 and underneath floor 22. In certain embodiments, ring 54 may comprise an inner layer disposed inside an outer layer such as dome 12.

Figure 7:
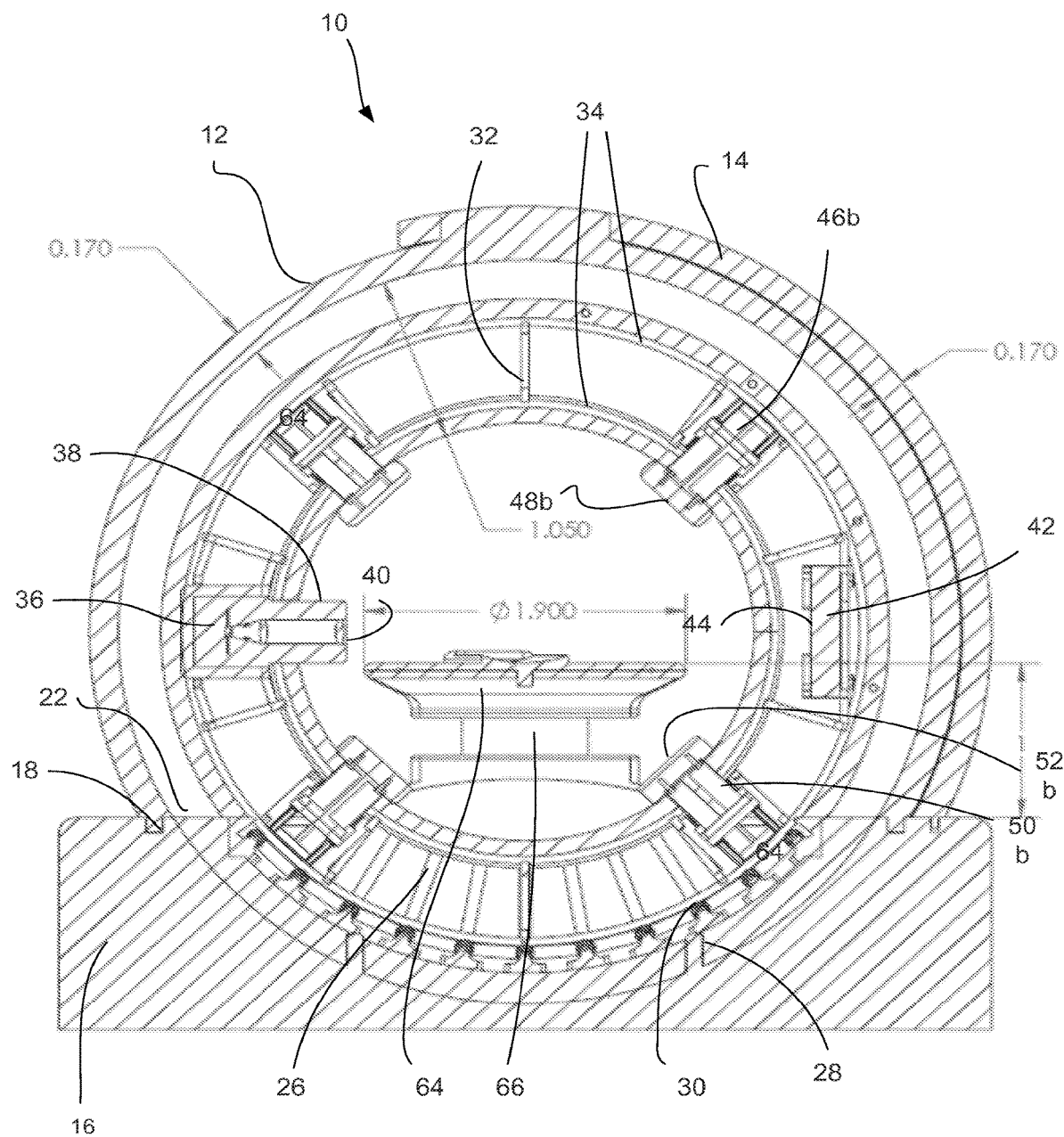
FIG. 7 depicts a side view of a combination of the outer layer, floor section, rail structure, treatment table, framework, and ring of FIGS. 2A-6B.

FIG. 7 shows a cross section of an exemplary embodiment of system 10. In the embodiment shown, dome 12 is coupled to base 16, with the bottom of dome 12 resting within base 16. Door 14 is disposed outside the outer surface of dome 12 and configured to rotate around (or at least partially around) dome 12. Ring 54 is contained inside dome 12 and a portion of the inner face of ring 54 is disposed in channel 24 underneath floor 22. In the embodiment shown, outer face 56 of ring 54 is stationary and is affixed to floor 22 at the edge of channel 24 via framework 26. In the embodiment shown, framework 26 comprises rolling mechanisms 30 disposed on the inner surface of framework 26 of channel 24. In the embodiment shown, rail structure 32 is disposed inside of ring 54 and configured to rotate around a horizontal axis within the outer portion of ring 54. In the embodiment shown, rail structure 32 passes underneath floor 22 and is configured to rotate by rolling on rolling mechanisms 30. Rail structure 32 may be coupled to a power source providing the power necessary for the rotation of rail structure 32.

In the embodiment shown, radiation delivery device 36, imaging sources 46, primary shielding device 42, and imaging panels 50 are intermittently coupled in a stationary manner to rail structure 32. In the embodiment shown, imaging sources 46a-b are intermittently disposed on one side of radiation delivery device 36 while imaging panels 50a-b are intermittently disposed on the other side of radiation delivery device 36. In alternative embodiments, imaging sources 46 and imaging panels 50a-b may be alternately coupled along rail structure 32. In the embodiment shown, imaging panels 50a-b are disposed opposite imaging sources 46a-b. In the embodiment shown, primary shielding device 42 is disposed opposite radiation delivery device 36. Collimator 38, imaging sources 46a-b, and imaging panels 50a-b are configured to protrude through openings 62 (shown in FIGS. 6A-B) disposed in inner face 60 of ring 54. In an alternative embodiment, collimator 38, imaging sources 46a-b, and imaging panels 50a-b may be disposed inside ring 54.

In the embodiment shown, rail structure 32 and inner face 60 of ring 54 are configured to rotate on a horizontal axis around treatment table 64. In the embodiment shown, treatment table 64 is configured in a horizontal position and coupled to floor 22 via one or more legs 66. Treatment table 64 may be centrally located within ring 54 and configured to rotate about a vertical axis. In alternative embodiments, treatment table 64 may be configured to move spatially in three dimensional directions or be coupled to a surface other than floor 22, such as an inner wall of dome 12 or an outer face 56 or side face 58 of ring 54. In the embodiment shown, radiation delivery device 36 and imaging sources 46a-b emit radiation onto treatment table 64. In the embodiment shown, as treatment table 64 rotates about a vertical axis and rail structure 32 rotates about a horizontal axis, a patient lying on treatment table 64 may receive radiation treatment from multiple directions and angles. These multiple directions and angles may be represented in steradians, or solid angle units. In the embodiment shown, a combination of the rotation of treatment table 64 and the rotation of rail structure 32 enables 4π steradians of radiation coverage to be applied to a patient situated at the isocenter.

Figure 8:
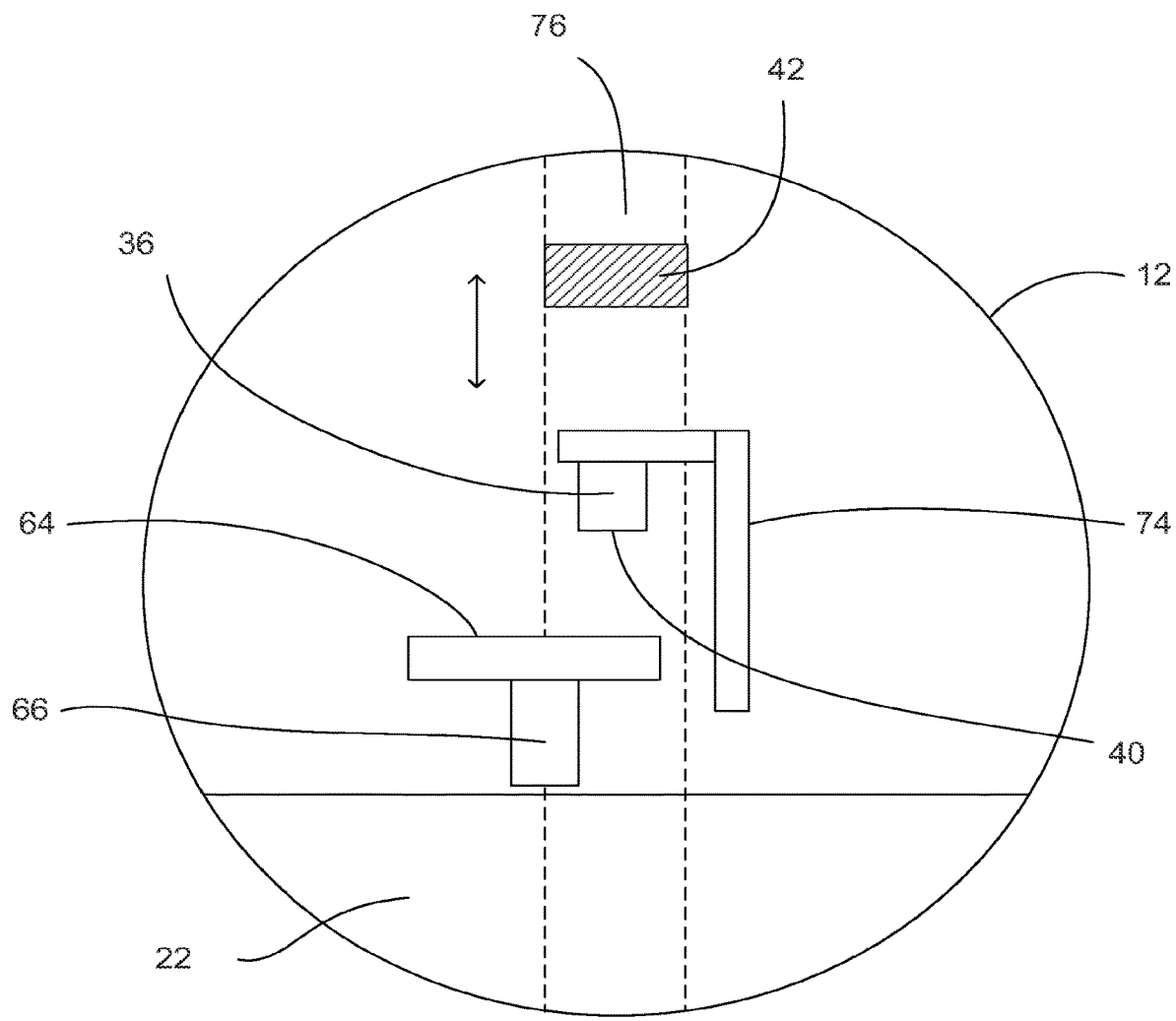
FIG. 8 depicts a side view of another embodiment of the disclosed systems.

FIG. 8 depicts a side, schematic view of a second embodiment of the disclosed systems. In the embodiment shown, radiation delivery device 36 is disposed inside dome 12. In the embodiment shown, dome 12 is configured as a secondary radiation shielding device. Radiation delivery device 36 may be coupled to arm 74. Radiation delivery device 36 may be disposed to rotate about a horizontal axis around treatment table 64. Treatment table 64 may be disposed to rotate about a vertical axis. In the embodiment shown, emission face 40 of radiation delivery device 36 is disposed to emit a radiation beam to the intersection of the rotational axes of treatment table 64 and radiation delivery device 36. Therefore, in the embodiment shown, as treatment table 64 rotates on a vertical axis and radiation delivery device 36 rotates on a horizontal axis, a patient lying on treatment table 64 may receive radiation treatment from multiple directions and angles.

In the embodiment shown, inner layer 76 is coupled to the inner surface of dome 12. Inner layer may comprise rail structure 32 (which may comprise, as explained above, one or more rails 34). In the embodiment shown, primary shielding device 42 is coupled to inner layer 76 and disposed to rotate around a horizontal axis. In the embodiment shown, primary shielding device 42 rotates to a position opposite emission face 40 of radiation delivery device 36. In doing so, primary shielding device 42 may rotate to a position underneath floor 22. This enables the primary shielding device 42 to absorb the primary radiation emitted from radiation delivery device 36. Primary shielding device 42 may rotate in synchrony with (or synchronously with) or independently of radiation delivery device 36.

Figure 9A:
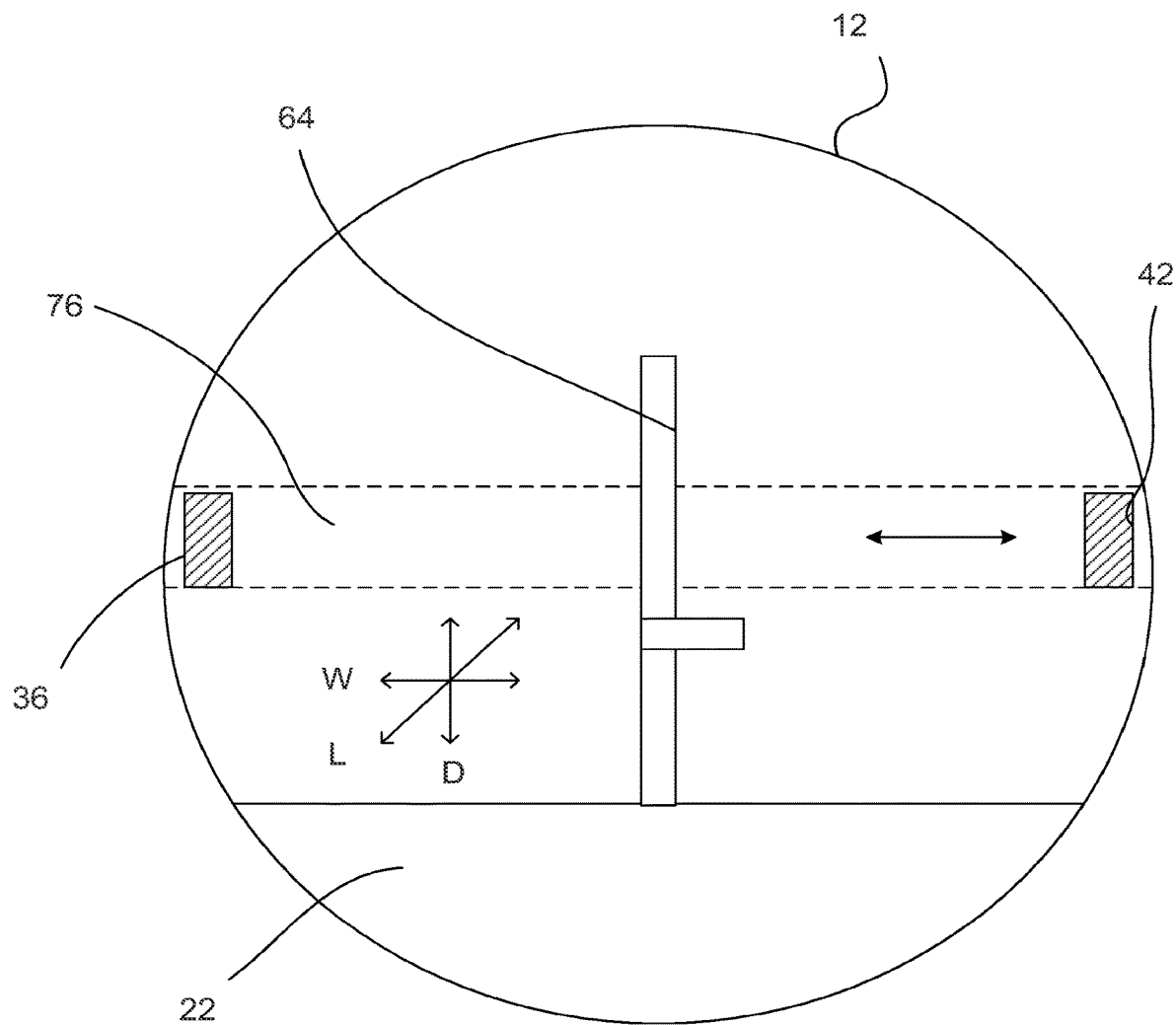
FIGS. 9A and 9B depict a side view and a top down view, respectively, of another embodiment of the disclosed systems.
Figure 9B:
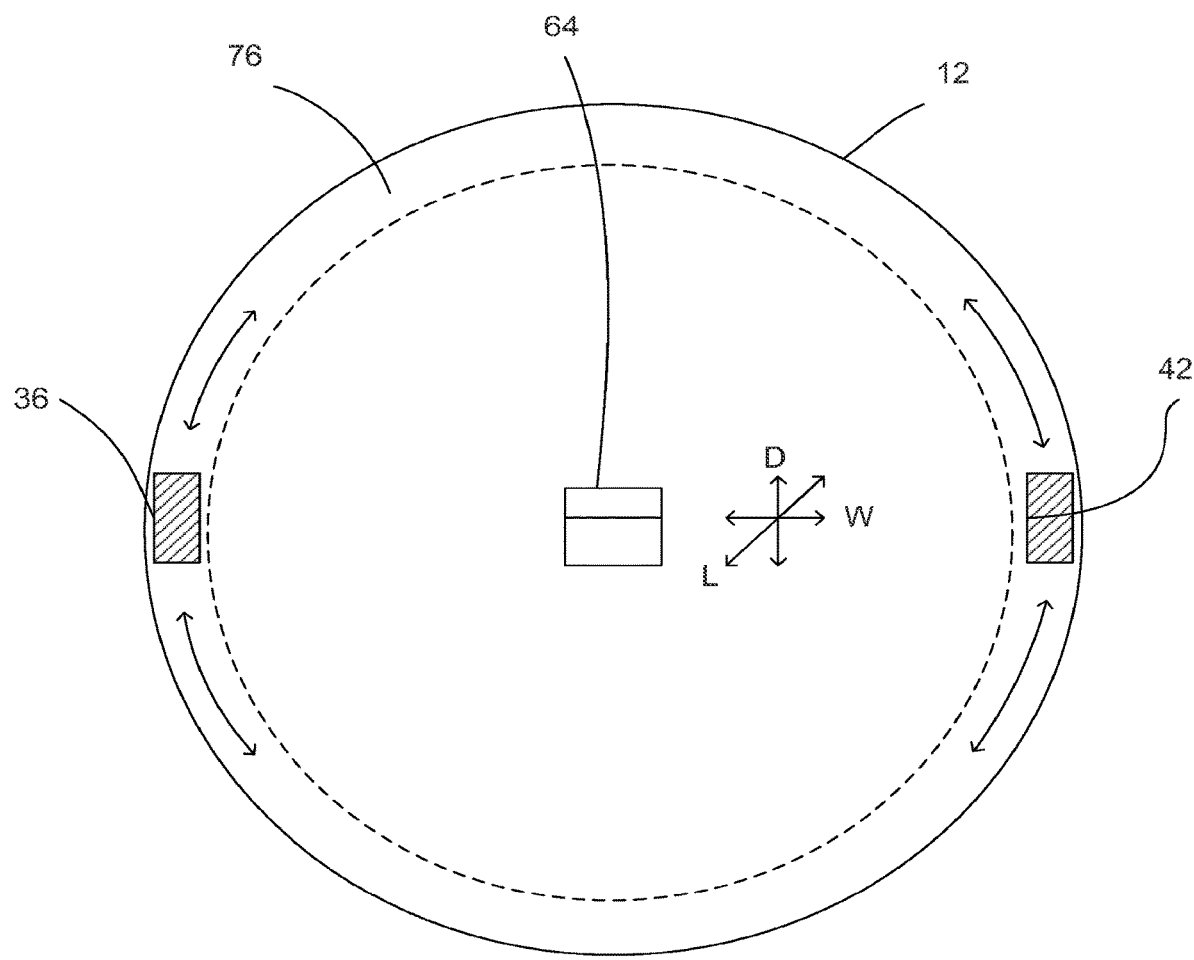

FIGS. 9A-B depict a side view and a top down view of a third embodiment of the disclosed systems. In the embodiment shown in FIGS. 9A-B, dome 12 is configured as a secondary radiation shielding device. In the embodiment shown, inner layer 76 is coupled to the inner surface of dome 12. Inner layer 76 may comprise rail structure 32 (which may comprise, as explained above, one or more rails 34). In the embodiment shown, radiation delivery device 36 and primary shielding device 42 are coupled to inner layer 76 and disposed to rotate around a vertical axis in a horizontal plane. The horizontal plane may coincide with the diameter of the dome 12. In the embodiment shown, primary shielding device 42 is disposed in a position opposite emission face 40 of radiation delivery device 36. This enables the primary shielding device 42 to absorb the primary radiation emitted from radiation delivery device 36. Primary shielding device 42 may rotate in synchrony with (or synchronously with) or independently of radiation delivery device 36.

In the embodiment shown, treatment table 64 may be disposed at the center of dome 12. In the embodiment shown, treatment table 64 is configured to slide in each of a lengthwise (L), widthwise (W), and depthwise (D) direction, as shown by arrows in FIGS. 9A-B. Therefore, in the embodiment shown, as treatment table 64 moves in three spatial directions, a patient lying on treatment table 64 may receive radiation treatment from multiple directions and angles.

Figure 10:
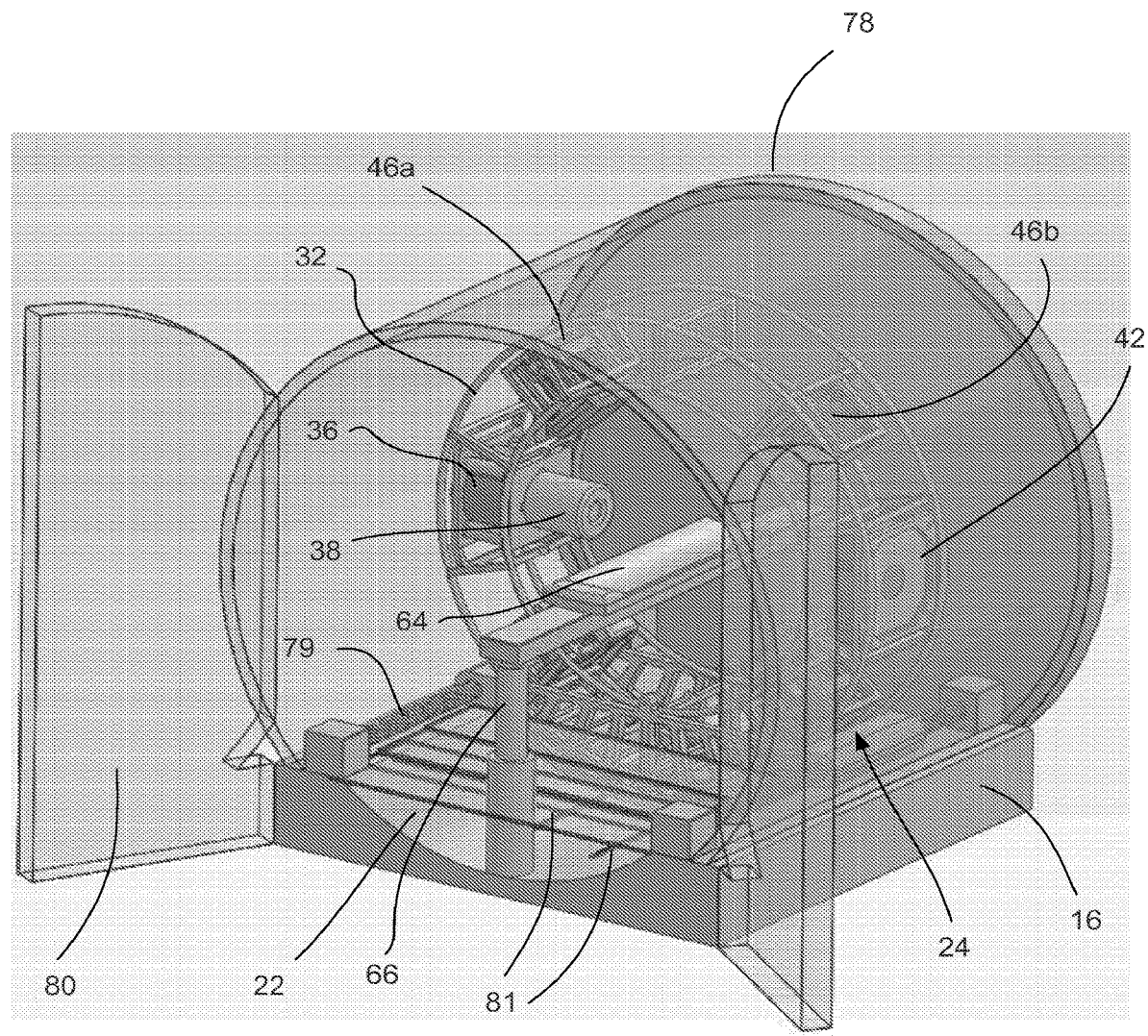
FIG. 10 depicts a perspective view of another embodiment of the disclosed systems.

FIG. 10 shows a fourth embodiment of the disclosed systems. In the embodiment shown in FIG. 10, the system's outer layer comprises a secondary radiation shield in the form of housing 78, which may be configured as a partial or complete cylinder (both of which may be characterized as cylinder-shaped) with at least one closable opening though which a patient and/or others may pass in preparation for radiation therapy. As shown in the depicted embodiment, the closable opening may be positioned at one end of the housing (though in other embodiments it may be located elsewhere), and housing 78 may comprise one or more doors 80 coupled to a central portion of the cylinder-shaped structure for opening/closing to thereby cover the closable opening; such doors may be disposed at one or both ends of housing 78. Housing 78, including doors 80, may comprise the same material(s) as dome 12 and door 14. In the embodiment shown, rail structure 32 is disposed inside housing 78 and coupled to framework 26. In the embodiment shown, framework 26 is disposed to move longitudinally along base 16, which is coupled to housing 78. In the embodiment shown, framework 26 moves via threaded bars 79 coupled to base 16 and along guides 18 disposed on the bottom surface of base 16. As rail structure 32 moves longitudinally, telescoping panels 81 disposed between threaded bars 79 may be configured to retract in a longitudinal direction toward doors 80. In the embodiment shown, radiation delivery device 36, imaging sources 46a-b, imaging panels 50a-b, and primary shielding device 42 are coupled to rail structure 32 and disposed to rotate around a horizontal axis passing through the center of rail structure 32. Rail structure 32 may be configured as shown in FIG. 4. In the embodiment shown, rail structure 32 is disposed within channel 24 and configured to rotate within channel 24 via rolling mechanisms 30. In the embodiment shown, primary shielding device 42 is disposed in a position opposite emission face 40 of radiation delivery device 36. This enables primary shielding device 42 to absorb the primary radiation emitted from radiation delivery device 36. Primary shielding device 42 may rotate in synchrony with (or synchronously with) radiation delivery device 36.

In the embodiment shown, treatment table 64 may be disposed on a horizontal axis at the longitudinal center of housing 78. In the embodiment shown, treatment table 64 is coupled to telescoping legs 66, which attach treatment table 64 to floor 22. In the embodiment shown, treatment table 64 is configured to move up and down in a vertical direction via legs 66. In the embodiment shown, treatment table 64 is further configured to move in a horizontal directions. In the embodiment shown, radiation delivery device 36 and primary shielding device 42 may rotate azimuthally on rail structure 32 as rail structure 32 moves longitudinally along the horizontal axis via threaded bars 79.

Figure 11:
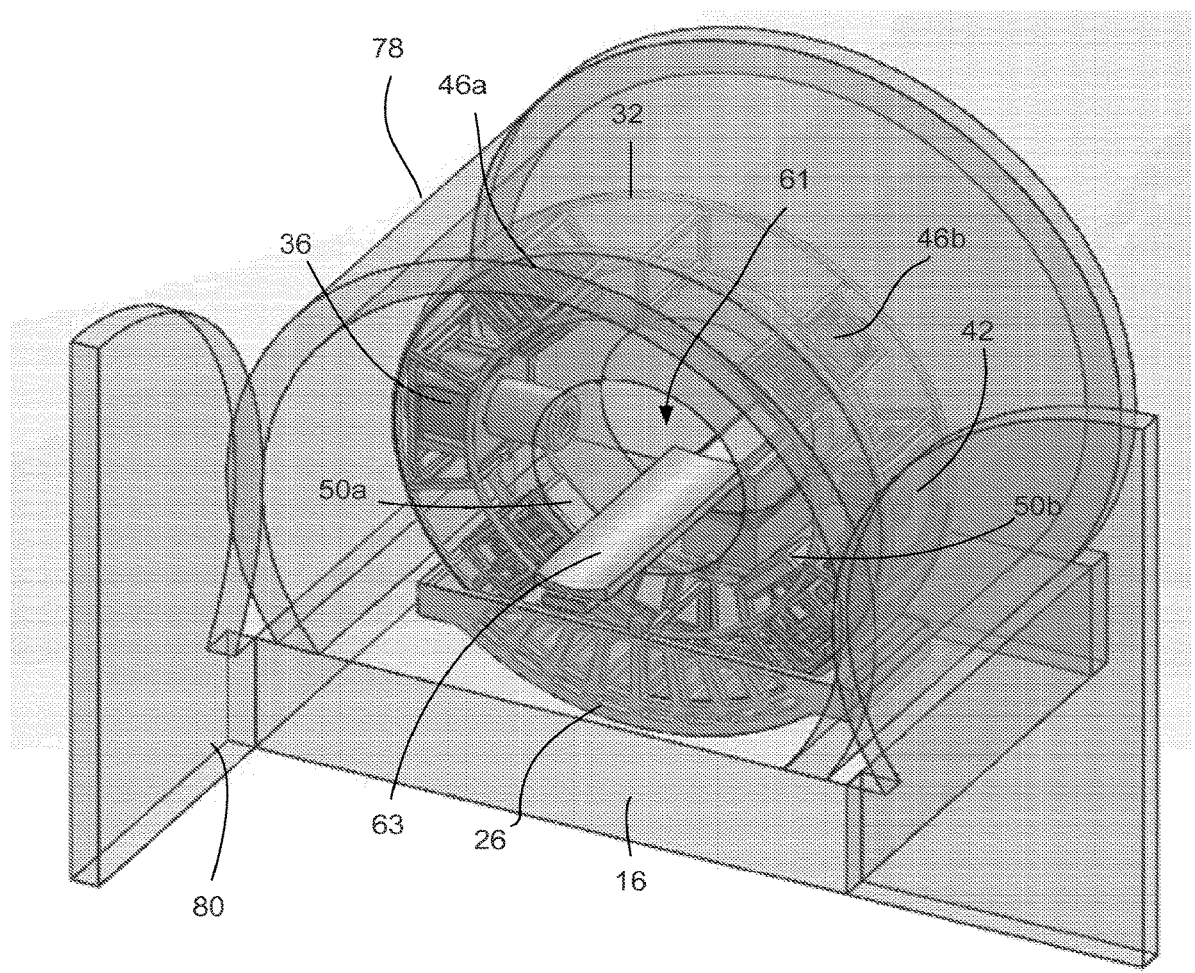
FIG. 11 depicts a perspective view of another embodiment of the disclosed systems.

FIG. 11 shows a fifth embodiment of the disclosed systems. In the embodiment shown in FIG. 11, the system's outer layer comprises a secondary radiation shield in the form of housing 78, which may be configured as a partial or complete cylinder (both of which may be characterized as cylinder-shaped) with at least one closable opening though which a patient and/or others may pass in preparation for radiation therapy. As shown in the depicted embodiment, the closable opening may be positioned at one end of the housing (though in other embodiments it may be located elsewhere), and housing 78 may comprise one or more doors 80 coupled to a central portion of the cylinder-shaped structure for opening/closing to thereby cover the closable opening; such doors may be disposed at one or both ends of housing 78. Housing 78, including doors 80, may comprise the same material(s) as dome 12 and door 14. In the embodiment shown, rail structure 32 is disposed inside housing 78 and coupled to framework 26.

In the embodiment shown, framework 26 is disposed in a fixed position within base 16. In some embodiments, framework 26 may be disposed centrally within housing 78. In the embodiment shown, radiation delivery device 36, imaging sources 46a-b, imaging panels 50a-b, and primary shielding device 42 are coupled to rail structure 32 and disposed to rotate around a horizontal axis passing through the center of housing 78. Rail structure 32 may be configured as shown in FIGS. 4-5. In the embodiment shown, primary shielding device 42 is disposed in a position opposite emission face 40 of radiation delivery device 36. This enables primary shielding device 42 to absorb the primary radiation emitted from radiation delivery device 36. Primary shielding device 42 may rotate in synchrony with (or synchronously with) radiation delivery device 36.

Figure 12:
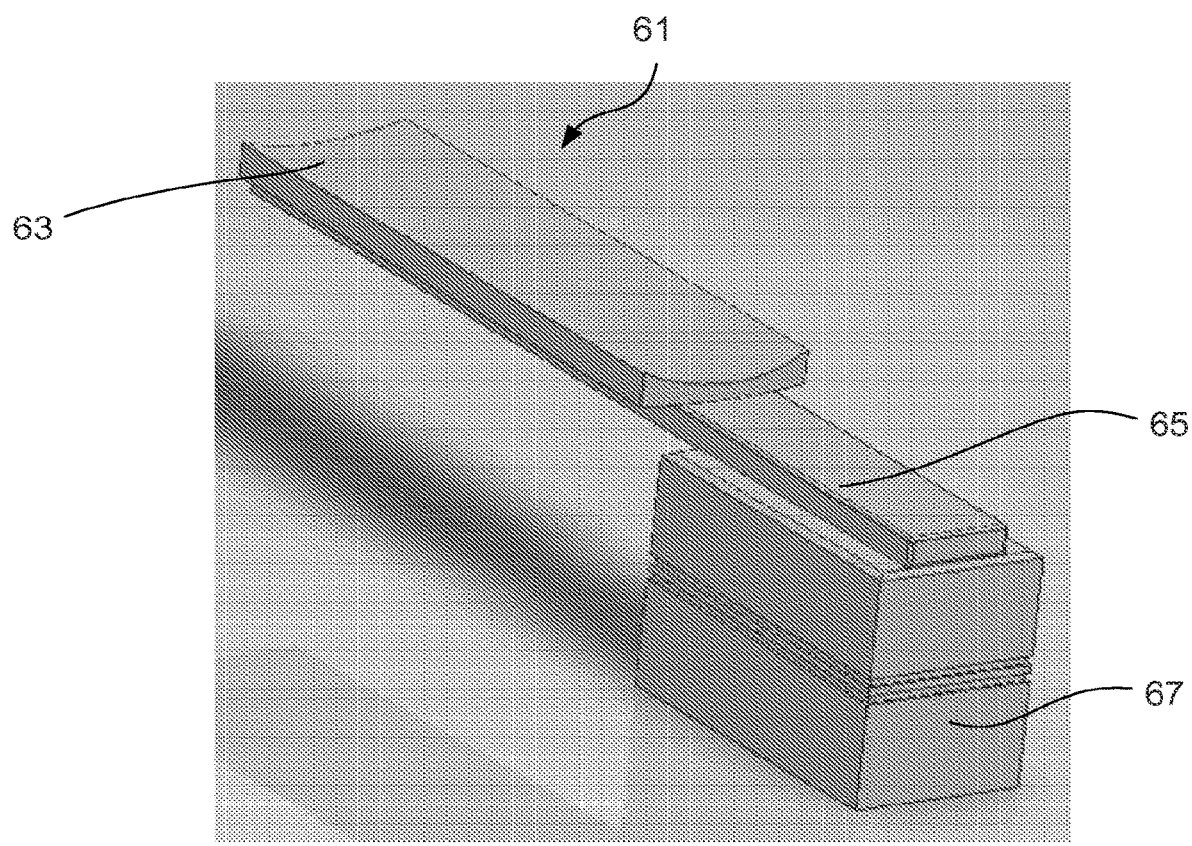
FIG. 12 depicts a slidable treatment table used in one or more of the disclosed systems.
Figure 13A:
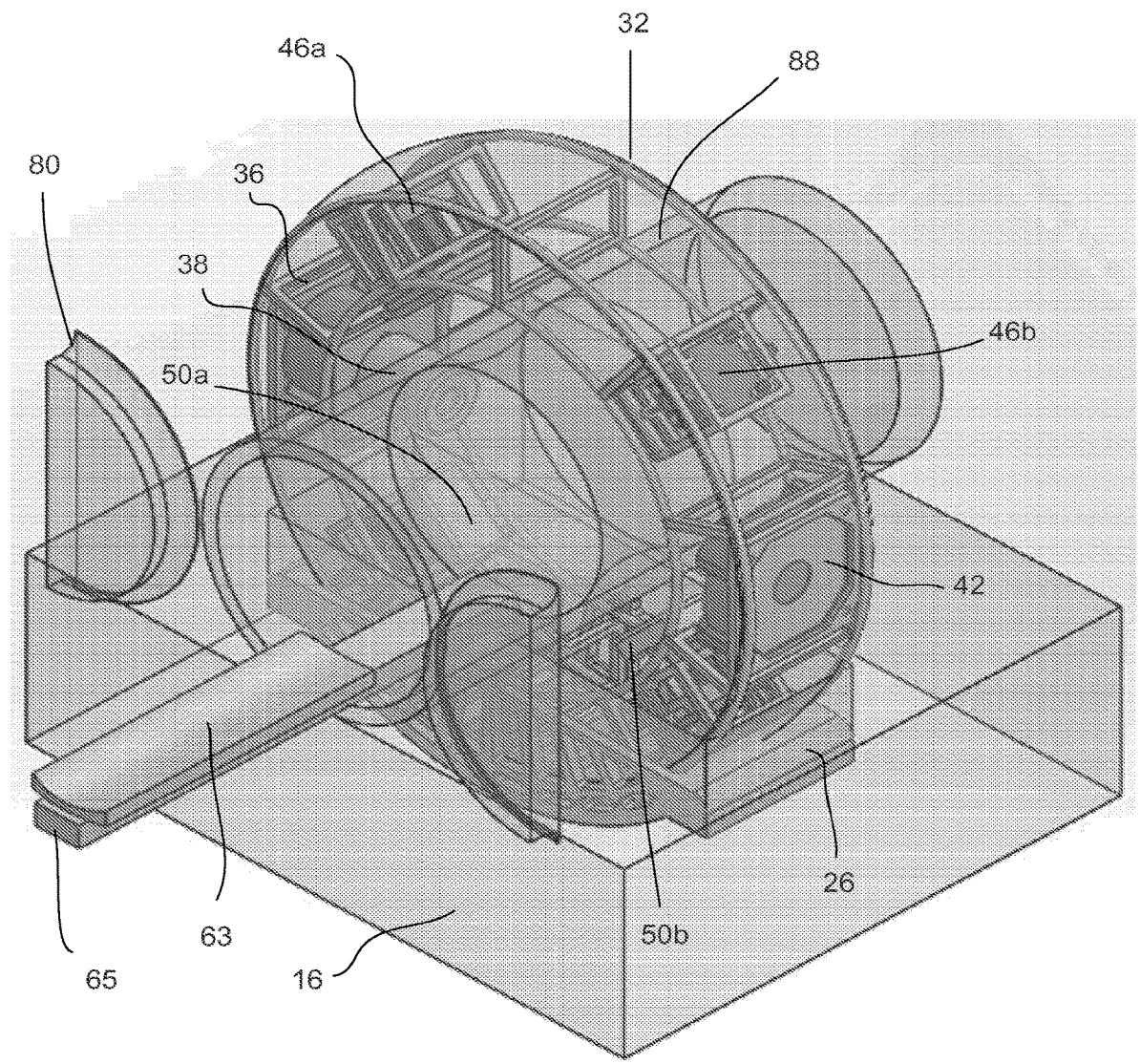
FIGS. 13A-13D depict a multiple perspective views and a top down view, respectively, of another embodiment of the disclosed systems.
Figure 13B:
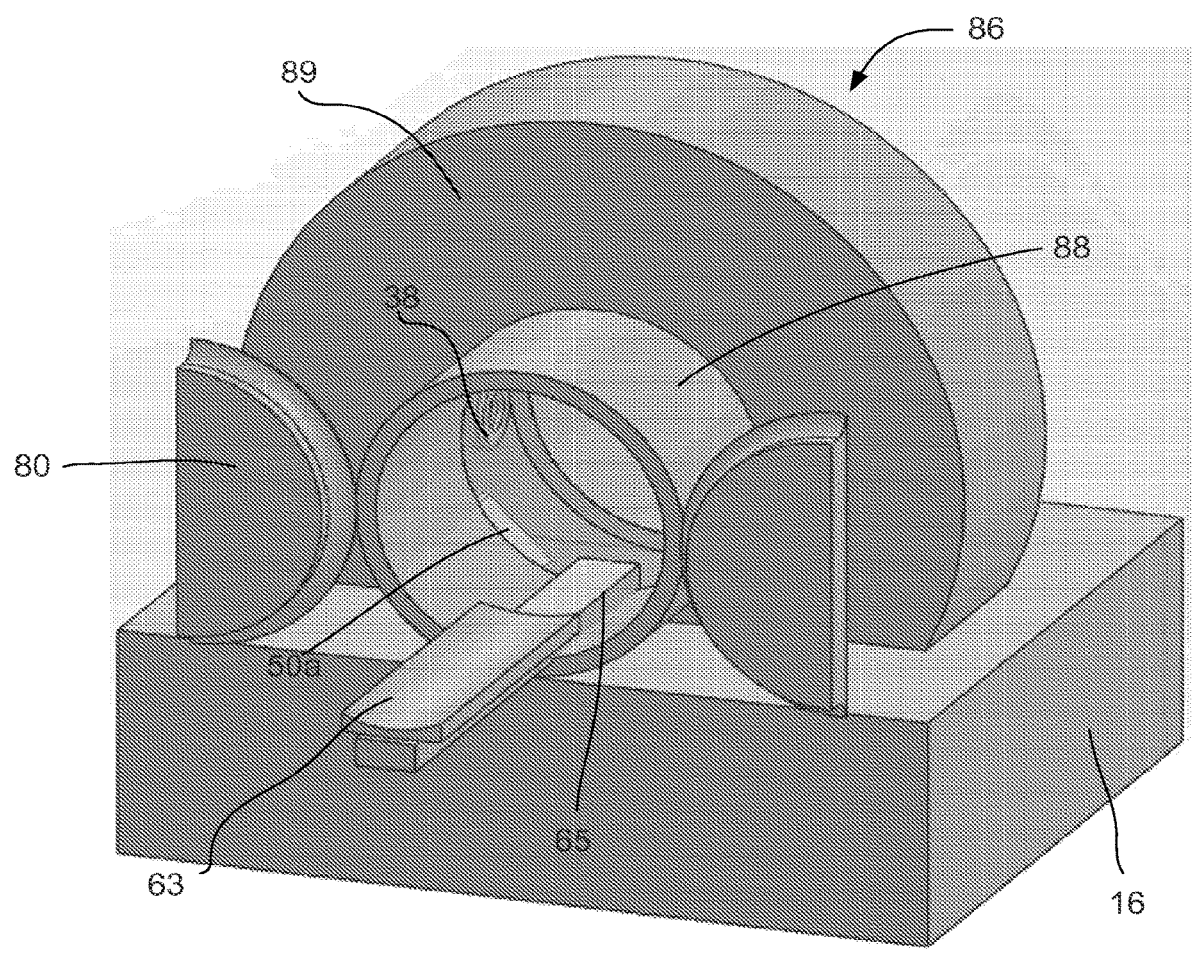
Figure 13C:
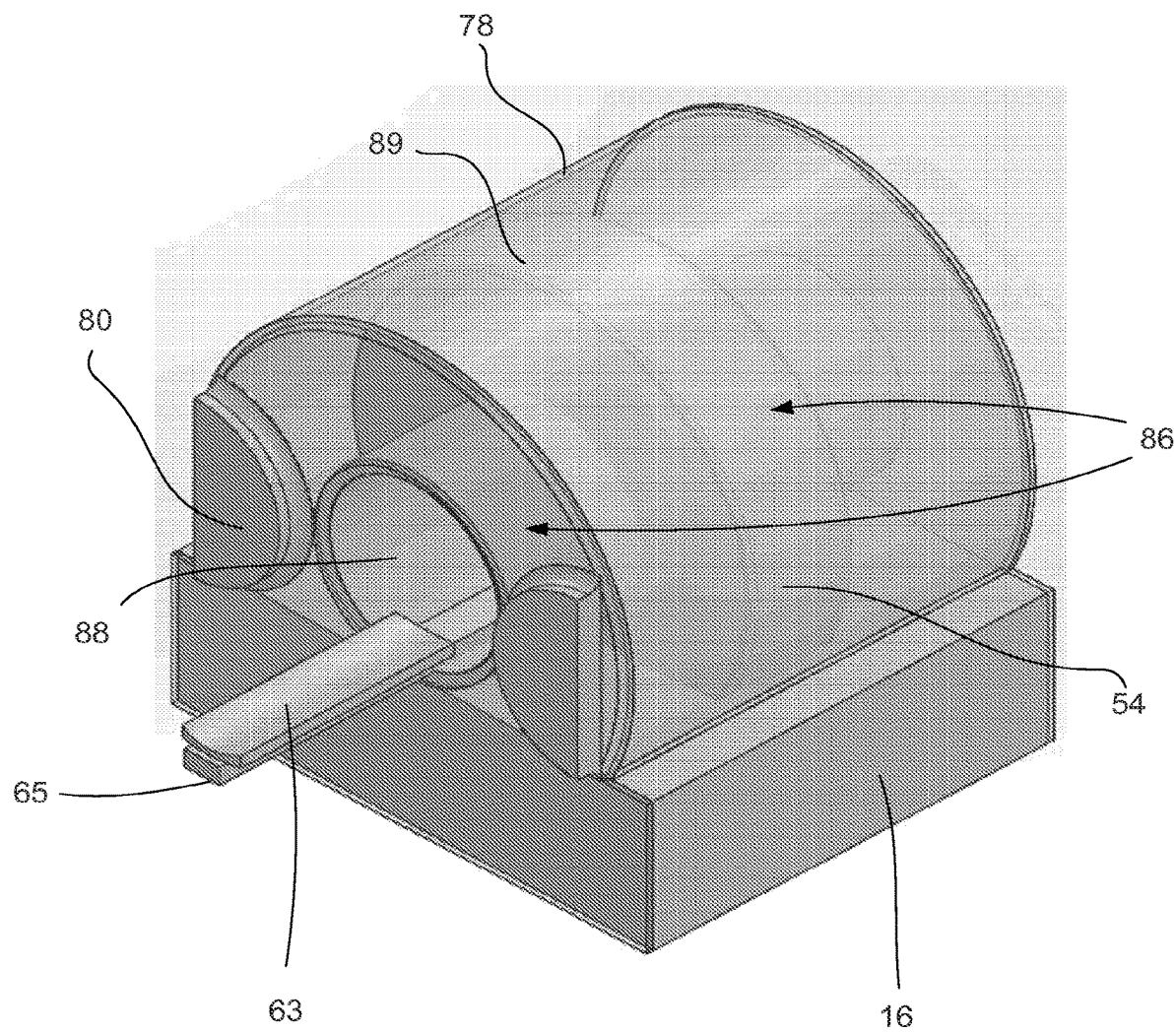
Figure 13D:
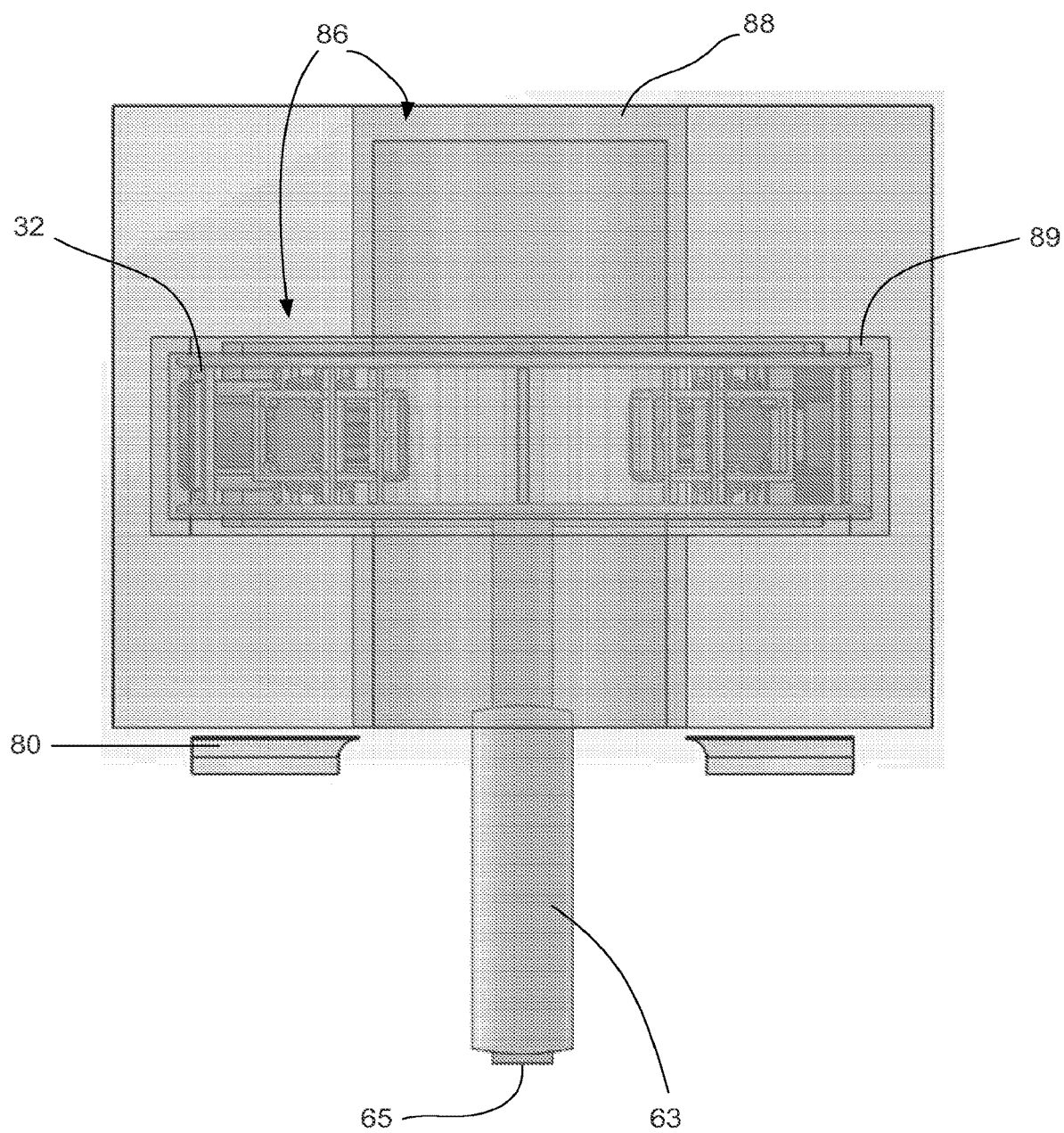

In the embodiment shown, the system includes a table system 61 that includes treatment table 63 that may be disposed on a horizontal axis at the longitudinal center of housing 78. As shown in FIG. 12, which illustrates the table system shown in FIG. 11, table system 61 also includes a treatment table guide 65 along which treatment table 63 may slide. Treatment table guide 65 may be configured to remain stationary. In the embodiment shown, table system 61 also includes pedestal 67 to which treatment table guide 65 is coupled (e.g., affixed), and pedestal 67 may be configured to remain stationary. In some embodiments, pedestal 67 may be affixed to floor 22. In some embodiments, pedestal 67 may be affixed beneath floor 22 and may protrude above floor 22. In some embodiments, pedestal 67 may be affixed to rear wall 85 of housing 78. In some embodiments, treatment table 63 of table system 61 is moveably affixed to treatment table guide 65 and configured to move longitudinally along a horizontal axis as well as vertically and laterally. In the embodiment shown, radiation delivery device 36 and primary shielding device 42 may rotate azimuthally on rail structure 32 as treatment table 63 moves longitudinally along the horizontal axis over treatment table guide 65.

FIGS. 13A-D show a sixth embodiment of the disclosed systems. In the embodiments shown in FIGS. 13A-D, the system's outer layer comprises a housing 78, which may be configured as a partial or complete cylinder (both of which may be characterized as cylinder-shaped) with at least one closable opening though which a patient may pass in preparation for radiation therapy. As shown in the depicted embodiment, the closable opening may be positioned at one end of the housing (though in other embodiments it may be located elsewhere), and housing 78 may comprise one or more doors 80 coupled to a central portion of the cylinder-shaped structure for opening/closing to thereby cover the closable opening; such doors may be disposed at one or both ends of housing 78. In the embodiment shown, rail structure 32 is disposed inside housing 78 and coupled to framework 26.

In the embodiment shown, framework 26 is disposed in a fixed position within base 16. In some embodiments, framework 26 may be disposed centrally within housing 78. In the embodiment shown, radiation delivery device 36, imaging sources 46a-b, imaging panels 50a-b, and primary shielding device 42 are coupled to rail structure 32 and disposed to rotate around a horizontal axis passing through the center of housing 78. Rail structure 32 may be configured as shown in FIGS. 4-5. In the embodiment shown, primary shielding device 42 is disposed in a position opposite emission face 40 of radiation delivery device 36. This enables primary shielding device 42 to absorb the primary radiation emitted from radiation delivery device 36. Primary shielding device 42 may rotate in synchrony with (or synchronously with) radiation delivery device 36.

In the embodiment shown, the system includes a table system that includes treatment table 63 that may be disposed on a horizontal axis at the longitudinal center of rail structure 32. In some embodiments, the table system, which may be like table system 61 but may lack pedestal 67, may include treatment table guide 65 along which treatment table 63 may slide. In some embodiments, treatment table guide 65 may be coupled (e.g., affixed) to modular shield 86 and configured to be stationary. In such embodiments, treatment table 63 may be moveably coupled to treatment table guide 65 and configured to move longitudinally along a horizontal axis as well as vertically and laterally. In some embodiments, treatment table 63 may be affixed in a stationary manner to treatment table guide 65. In such embodiments, treatment table guide 65 is configured to be movably coupled to modular shield 86 and can slide on a horizontal axis.

In the embodiments shown in FIGS. 13A-D, modular shield 86 comprises a cylinder portion 88 and a ring portion 89 and acts as a secondary shielding device. In the embodiment shown, cylinder portion 88 and ring portion 89 are situated around treatment table 63 and rail structure 32, respectively. Therefore, the secondary shielding of the system of this embodiment is reduced azimuthally as compared to other embodiments described herein. In the embodiment shown, cylinder portion 88 is disposed in a cylinder shape and extends along the longitudinal center of housing 78. In the embodiment shown, cylinder portion 88 comprises a gap having a width of rail structure 32. In the embodiment shown, the gap in cylinder portion 88 is configured to avoid obstructing the movement of collimator 38, imaging sources 46a-b, imaging panels 50a-b, and primary shielding device 42 as rail structure 32 rotates. In some embodiments, treatment table 63 may be positioned over the gap. In such a configuration, the gap in cylinder portion 88 enables radiation emitted from collimator 38 to reach a patient lying on treatment table 63.

In the embodiment shown in FIGS. 13A-D, ring portion 89 of modular shield 86 has a partial ring shape and is disposed within housing 78 to cover the outside surfaces of rail structure 32. In the embodiment shown, rail structure 32 is disposed to rotate freely within ring portion 89. In the embodiment shown, ring portion 89 is coupled to cylinder portion 88 at both sides of the gap in cylinder portion 88 to form modular shield 86. In the embodiment shown, ring portion 89 is further coupled to the top of base 16. In the embodiment shown in FIG. 13A, collimator 38, imaging sources 46a-b, imaging panels 50a-b, and primary shielding device 42 are disposed inside ring portion 89.

In the embodiments shown, radiation delivery device 36 and primary shielding device 42 may rotate azimuthally on rail structure 32 as treatment table 63 moves longitudinally along a horizontal axis over treatment table guide 65.

Figure 14A:
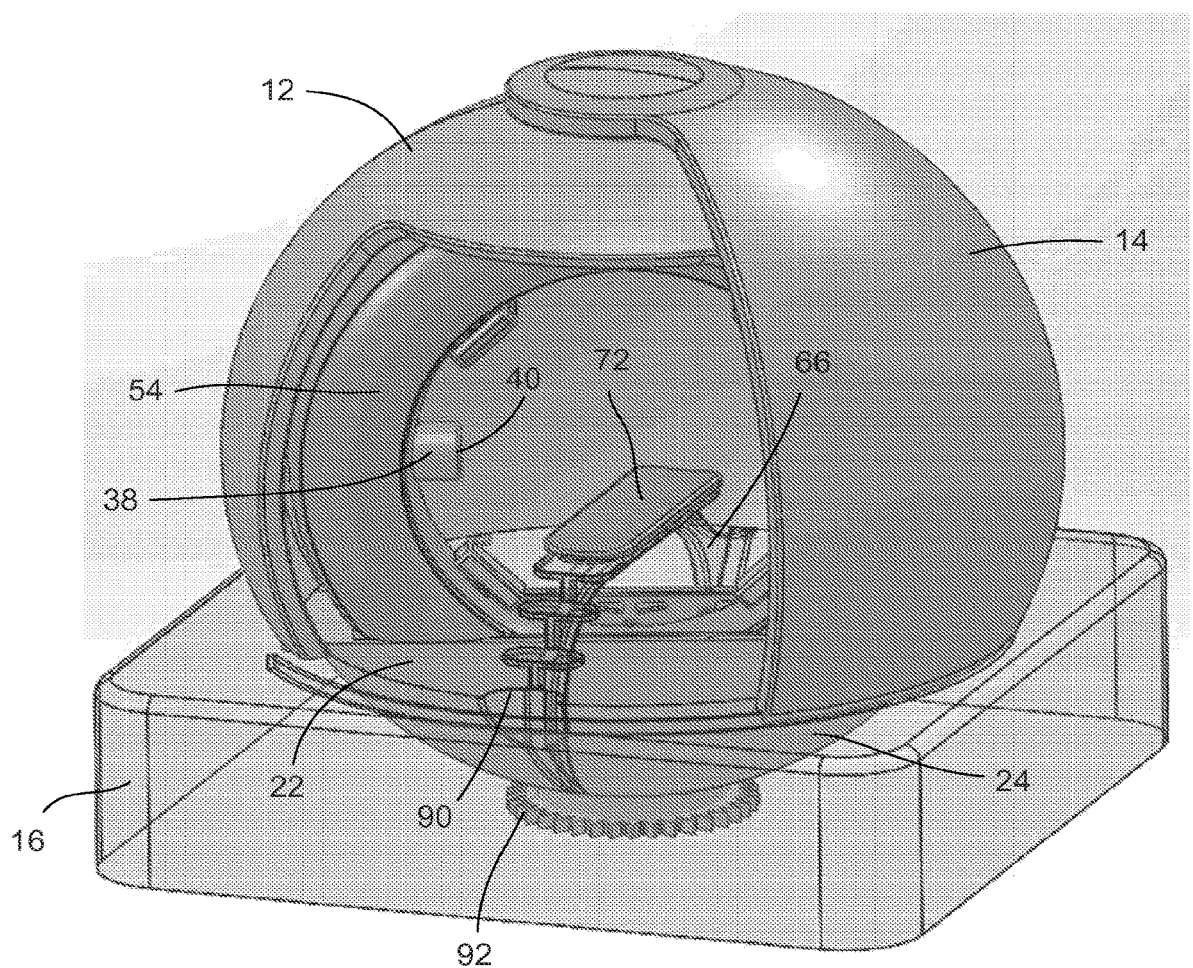
FIGS. 14A-14C depict a perspective view, a side view, and a front view, respectively, of a another embodiment of the disclosed systems.
Figure 14B:
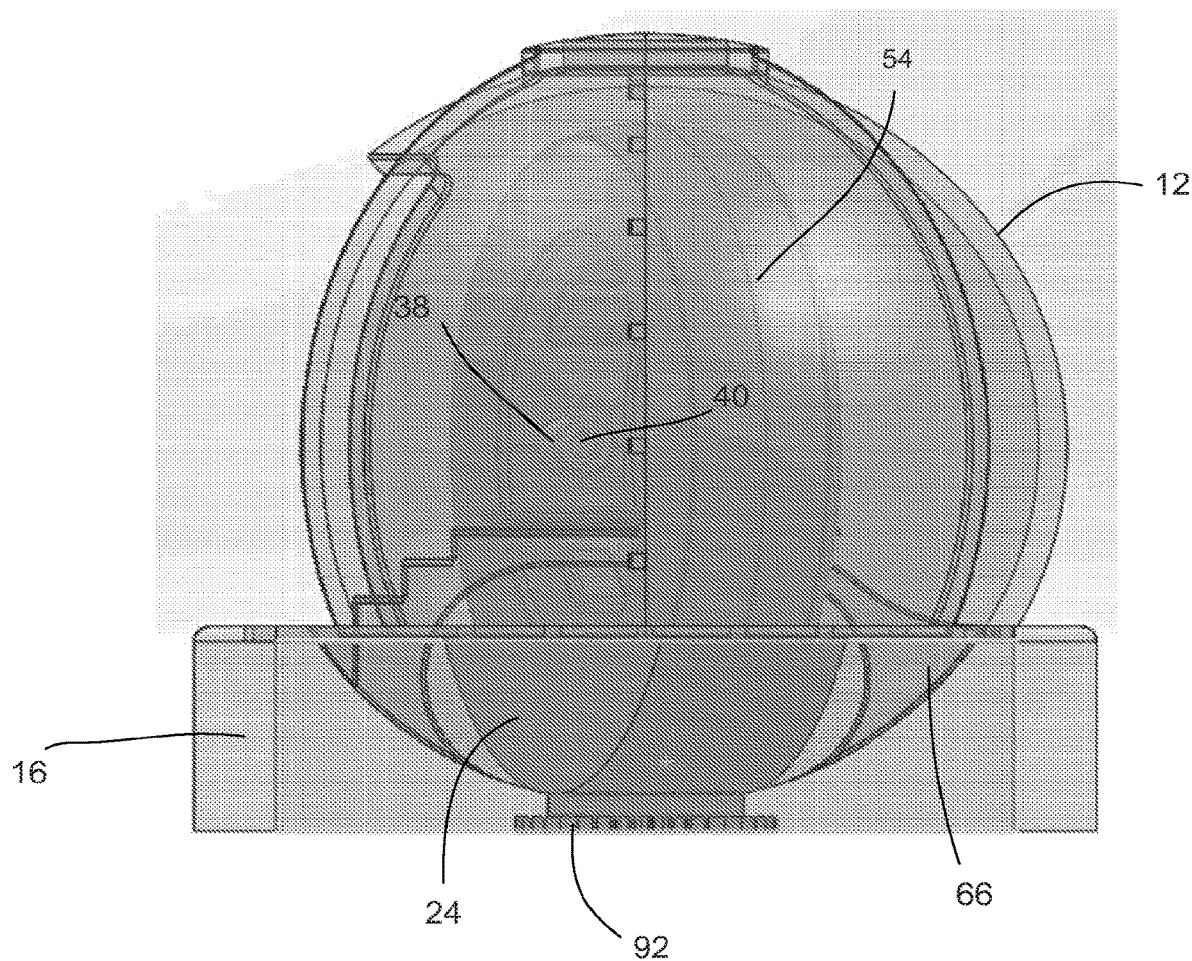
Figure 14C:
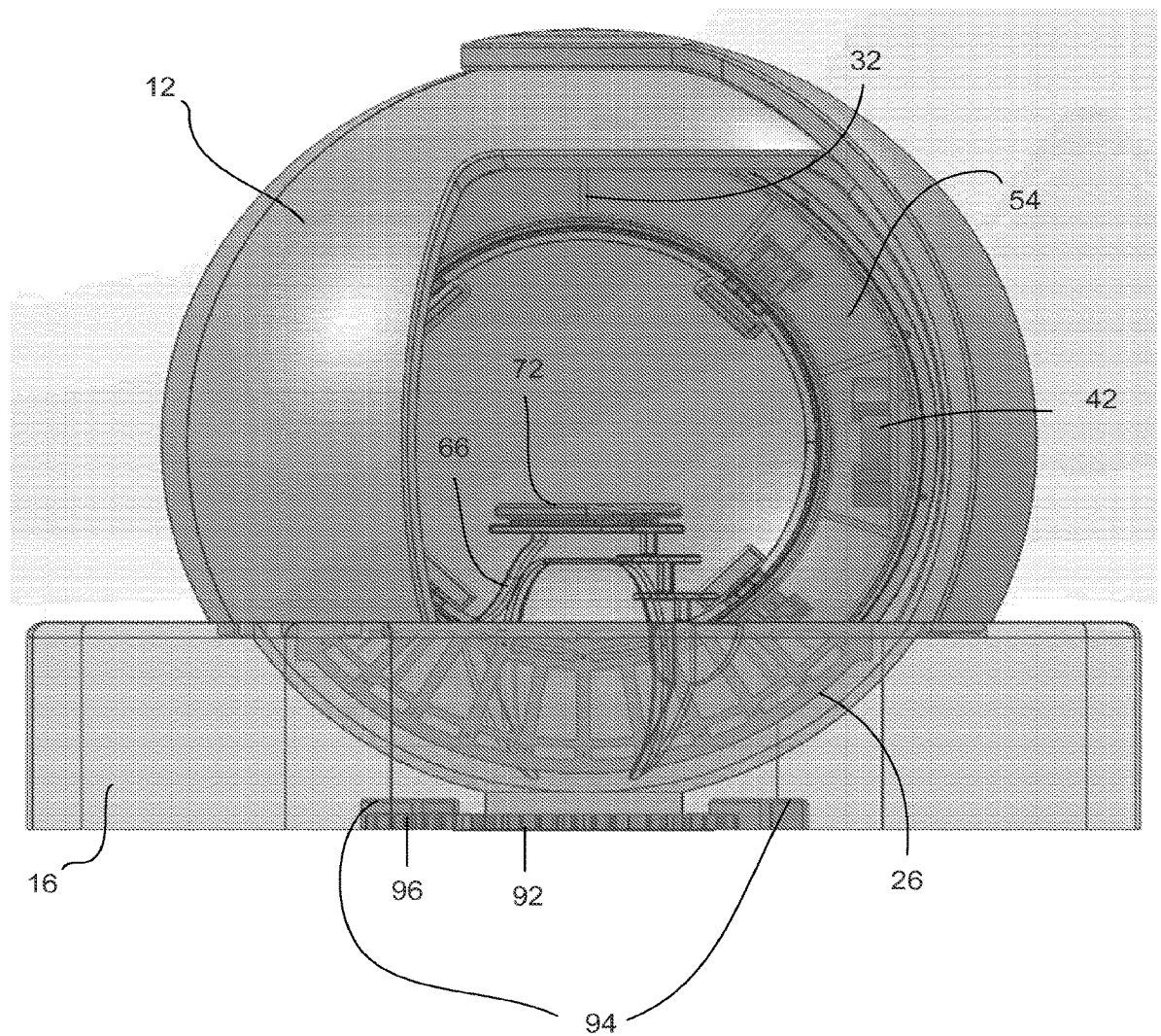

FIGS. 14A-C shows a seventh embodiment of the disclosed systems. In the embodiment shown, modular dome 12, door 14, and base 16 comprise the secondary shielding layer of the system. In the embodiment shown, bed 72 of the system is disposed at an isocenter of dome 12 and is coupled to one or more legs 66. In the embodiment shown, one or more legs 66 couple bed 72 to the surface of base 16 in a stationary position. In some embodiments, bed 72 may be configured to move in three spatial directions. In some embodiments, the three spatial directions may be lengthwise, widthwise, and depthwise.

In the embodiment shown, openings 90 are situated in floor 22 and disposed on both sides of channel 24. In the embodiment shown, legs 66 extend below floor 22 through openings 90 to the surface of base 16. In the embodiment shown, floor 22 is configured to be partially movable about a vertical axis. In the embodiment shown, openings 90 are large enough to accommodate a movement of floor 22 associated with a rotation of ring 54 about the vertical axis.

In the embodiment shown, the system includes primary gear 92, which is disposed horizontally within base 16 (and outside dome 12) and firmly coupled (e.g., attached, by welding for example) to framework 26 or ring 54. In the embodiment shown, gear 92 is configured to partially rotate about a vertical axis. In the embodiment shown in FIG. 14B, as gear 92 rotates, channel 24 rotates, resulting in ring 54 rotating about the same vertical axis as gear 92. In the embodiment shown, floor 22 abuts framework 26 and rotates as ring 54 rotates. In the embodiment shown, the system includes one or more motors 94 that are coupled to one or more secondary gears 96. In the embodiment shown in FIG. 14C, secondary gears 96 are powered by motors 94 to partially rotate about respective vertical axes (that are parallel to the axis about which gear 92 can rotate). In the embodiment shown, secondary gears 96 are coupled to primary gear 92. In the embodiment shown, as secondary gears 96 rotate, they drive primary gear 92 to rotate.

In the embodiment shown, rail structure 32 is disposed within ring 54 and may be configured as shown in FIGS. 4-5. In the embodiment shown, primary shielding device 42 is disposed in a position opposite emission face 40 of collimator 38. This enables primary shielding device 42 to absorb the primary radiation emitted from collimator 38. Primary shielding device 42 may rotate in synchrony with (or synchronously with) collimator 38. In the embodiment shown, the rotation of ring 54 about the vertical axis combined with the rotation of rail structure 32 about the horizontal axis enables radiation to be applied to a patient on bed 72 may many different angles.

In some embodiments, the disclosed secondary radiation shields are configured as mobile units that will be unconnected to the structural framework of the buildings in which they can be used. They can substantially cover the disclosed treatment tables, rings, and radiation delivery devices. As a result, leakage radiation produced by the radiation delivery devices and not intended for therapeutic usage should not be able to breach the secondary radiation shield. Therefore, anyone outside the secondary radiation shield should not be materially affected by primary or secondary radiation.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the disclosed devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A radiation therapy apparatus, comprising
    an inner layer comprising:
        a radiation delivery device configured to emit primary radiation;
        a primary radiation shielding device configured to receive the primary radiation;
        one or more rails mounted on an inner surface of the inner layer, wherein the radiation delivery device and the primary radiation shielding device are disposed on the one or more rails; and
        a treatment table disposed inside the one or more rails, wherein the treatment table is configured to rotate around the vertical axis and the one or more rails are configured to rotate 360 degrees around the treatment table to deliver $4\pi$ steradians of radiation coverage to a patient positioned on the treatment table; and
    an outer layer comprising a secondary radiation shielding device integrated into the radiation therapy apparatus and configured to block secondary radiation, the secondary radiation shielding device comprising:
        a cylinder-shaped portion;
        a ring-shaped portion, the ring-shaped portion disposed to cover the radiation delivery device, and the primary radiation shielding device; and
        a housing configured to cover the secondary shielding device.

2. The apparatus of claim 1, wherein the one or more rails are disposed in a circular shape and configured to rotate around a horizontal axis.

3. The apparatus of claim 2, wherein the primary radiation shielding device is disposed opposite the radiation delivery device.

4. The apparatus of claim 1, wherein the apparatus is configured so that the radiation delivery device and the primary radiation shielding device rotate around a horizontal axis in synchrony with each other.

5. The apparatus of claim 1, wherein the housing is dome-shaped.

6. The apparatus of claim 1, wherein the housing is cylinder-shaped.

7. The apparatus of claim 1, wherein the primary radiation shielding device is configured to block at least 99.9% of radiation incident upon the primary radiation shielding device.

8. The apparatus of claim 1, wherein the secondary radiation shielding device is configured to block at least 99.9% of radiation incident upon the secondary radiation shielding device.

9. The apparatus of claim 1, wherein the cylinder shaped portion includes a closable opening through which a patient may pass in preparation for radiation therapy.

10. The apparatus of claim 9, wherein the cylinder shaped portion includes one or more doors coupled to a central portion of the cylinder shaped portion, the one or more doors covering and opening the closeable opening.

11. The apparatus of claim 1, further comprising one or more imaging sources and one or more imaging panels.

12. The apparatus of claim 11, wherein the one or more imaging sources and the one or more imaging panels are coupled to the one or more rails.

13. The apparatus of claim 11, wherein the one or more imaging sources and the one or more imaging panels are disposed inside the ring shaped portion.

14. The apparatus of claim 1, wherein the cylinder-shaped portion extends along the longitudinal center of the housing within the one or more rails.

15. The apparatus of claim 14, wherein the treatment table is movable and configured to slide inside the cylinder shaped portion.

16. The apparatus of claim 15, further comprising a gap in the cylinder shaped portion having the width of the one or more rails, the gap configured to avoid obstructing movement of the radiation delivery device and the primary radiation shielding device as the radiation delivery device and the primary radiation shielding device rotate around the horizontal axis.

17. The apparatus of claim 16, wherein the cylinder-shaped portion is configured to receive a portion of the treatment table within the gap to enable radiation emitted from the radiation delivery device to reach the patient positioned on the portion of the treatment table within the gap.

18. The apparatus of claim 16, wherein the ring shaped portion is coupled to the cylinder shaped portion at both sides of the gap.

19. The apparatus of claim 16, wherein the treatment table is configured to move between a first position over the gap and a second position away from the gap.

20. The apparatus of claim 1, wherein the steradians are solid angle units describing a direction of primary radiation applied to the patient disposed on the treatment table.

* * * * *